US005831057A

United States Patent [19]
Tully et al.

[11] Patent Number: 5,831,057
[45] Date of Patent: Nov. 3, 1998

[54] ASSOCIATIVE LEARNING AND THE LINOTTE GENE

[75] Inventors: Timothy Tully, Cold Spring Harbor; Gert M. Bolwig, Syosset, both of N.Y.

[73] Assignee: Cold Spring Harbor Laboratory, Cold Spring Harbor, N.Y.

[21] Appl. No.: 723,585

[22] Filed: Oct. 1, 1996

Related U.S. Application Data

[60] Provisional application No. 60/004,845 Oct. 5, 1995.
[51] Int. Cl.$^6$ ..................................................... C12N 15/12
[52] U.S. Cl. .......................................... 536/23.5; 536/23.1
[58] Field of Search .................................... 536/23.1, 23.5

[56] References Cited

PUBLICATIONS

DeZazzo and Tully, "Dissection of Memory Formation: From Behavioral Pharmacology To Molecular Genetics", *Trends Neurosci.*, 18(5):212–217 (1995).
Hammer and Menzel, "Learning and Memory in the Honeybee", *J. Neurosci.*, 15(3):1617–1630 (1995).
Tully, T., et al., "Genetic Dissection of Memory Formation in *Drosophila Melanogaster*", *Cold Spring Harbor Symp. Quant. Biol.*, 55:203–211 (1990).
Davis and Squire, "Protein Synthesis and Memory: A Review", *Psychological Bulletin*, 96(3):518–559 (1984).
Castellucci, V.F., et al., "Inhibitor of Protein Synthesis Blocks Long–Term Behavioral Sensitization in the Isolated Gill–Withdrawal Reflex of Aplysia", *J. of Neurobio.*, 20(1): 1–9 (1989).
Crow and Forrester, "Inhibition of Protein Synthesis Blocks Long–Term Enchancement of Generator Potentials Produced by One–Trial in vivo Conditioning in Hermissenda", *Proc. Natl. Acad. Sci., USA*, 87:4490–4494 (1990).
Tully, T., et al., "Genetic Dissection of Consolidated Memory in Drosophila", *Cell*, 79:35–47 (1994).
Carew, T.J., et al., "Long–Term Habituation of a Defensive Withdrawal Reflex in Aplysia", *Science*, 175:451–454 (1972).
Frost, W., et al., "Monosynaptic Conncections Made by the Sensory Neurons of the Gill– and Siphon–Withdrawal Reflex in Aplysia Participate in the Storage of Long–Term Memory for Sensitization", *Proc. Natl. Acad. Sci. USA*, 82:8266–8269 (1985).
Huang, Y–Y., et al., "Recruitment of Long–Lasting and Protein Kinase A–dependent Long–Term Potentiation in the CA 1 Region of Hippocampus Requires Repeated Tetanization", *Learning and Memory* 1:74–82 (1994).
Alberini, C., et al., "C/EBP Is An Immediate–Early Gene Required for the Consolidation of Long–Term Facilitation in Aplysia", *Cell* 76:1099–1114 (1994).
Bourtchuladze, R., et al., "Deficient Long–Term Memory in Mice with a Targeted Mutation of the cAMP–Responsive Element–Binding Protein", *Cell*, 79:59–68 (1994).

Yin, J. C. P., et al., "Induction of a Dominant Negative CREB Transgene Specifically Blocks Long–Term Memory in Drosophila", *Cell*, 79:49–58 (1994).
Tully and Quinn, "Classical Conditioning and Retention in Normal and Mutant *Drosophila Melanogaster*", *J. Comp. Physiology A* 157:263–277 (1985).
Tully and Gold, "Differential Effects of Dunce Mutations on Associative Learning and Memory in Drosophila", *J. Neurogenetics*, 9:55–71 (1993).
Boynton and Tully, "latheo, a New Gene Involved in Associative Learning and Memory in *Drosophila Melanogaster*, Identified from P Element Mutagenesis"*Genetics*, 131:655–672 (1992).
Dura, J. –M., et al., "Identification of Linotte, A New Gene Affecting Learning and Memory in *Drosophila Melanogaster*", *J. Neurogenetics*, 9:1–14 (1993).
Ewer, J., et al., "An Inducible Promoter Fused to the Period Gene in Drosophila Conditionally Rescues Adult Per–Mutant Arrhythmicity", *Nature*, 333:82–84 (1988).
Dauwalder and Davis, "Conditional Rescue of the dunce Learning/Memory and Female Fertility Defects with Drosophila or Rat Transgenes", *J. of Neuroscience*, 15(5) :3490–3499 (1995).
Hawkins and Kandel, "Is There A Cell–Biological Alphabet for Simple Forms of Learning?", *Psychological Review*, 91(3) :375–391 (1984).
Davis, R., "Mushroom Bodies and Drosophila Learning", *Neuron*, 11:1–14 (1993).
Bliss and Collingridge, "A Synaptic Model of Memory: Long–Term Potentiation in the Hippocampus," *Nature*, 361:31–39 (1993).
Bryne J., et al., "Roles of Second Messenger Pathways in Neuronal Plasticity and in Learning and Memory", *Advances in Second Messenger and Phosphoprotein Research*, 27:47–108 (1993).
Maurice Dura, J. et al., "The Drosophila learning and memory gene linotte encodes a putative receptor tyrosine kinase homologous to the human RYK gene product", *FEBS Letters 370*:250–254 (1995).
DeZazzo and Tully, "Dissection of memory formation: from behavioral pharmacology to molecular genetics", *TINS 18 (5)* :212–218 (1995).
Bolwig, G. et al., "Molecular Cloning of linotte in Drosophila: A Novel Gene That Functions in Adults during Associative Learning", *Neuron 15*:829–842 (1995).

*Primary Examiner*—Johnny F. Railey, II
*Attorney, Agent, or Firm*—Hamilton, Brook, Smith & Reynolds, P.C.

[57] ABSTRACT

The invention pertains to a novel gene present in cytological region 37D of the second chromosome which functions in associative learning and/or memory. Disruption of the gene, such as by P element transposon-tagged insertion, results in decreased associative learning and/or memory. The invention also pertains to a novel protein encoded by the gene, antibodies which bind the encoded protein, and homologs of the novel gene which function in associative learning and hybridize to the DNA sequence of the novel gene.

4 Claims, 6 Drawing Sheets

```
CTGAGAAGCGCGCAACGTGCACACTGGCAGGCTGATTGAAAAAATTCGTTGCAAATGTTT
ATGTACAAATATTGAATAAAAAATAAAAATGCTGCGGCAGGAGAACTTGGCAGCCAACTT
CTGCGGTCTCCTGGCCAGCCAGGGCTATAAAGAGAAGGCAAACGAGTGGCGCATTTTGGG
CCAGGAACAGGATGGATCTCTGCTCACGTCCTGGATATTCGAGTACGCGGACGAGGATCA
GCGCAAGGAGACGTGCATTGGCCACTTTCACGCCACCAAGAAGCAGCTGCGACTCCTTTG
GACCCTCGACAATTGCCGTGAGATCGTCCAGGCAACGATTAACAGCAGTGTCACATTGCT
GTCCTTCGTGGAGAAAACTGAGGGCAAGCTCTATCAGGCCTTTGTCGTGGAGGTAAGGAG
CTCCGAAGGTGGCACGGCCACGCCCCTCAACTCGGAGCCCTCCAACCGCCAGATGATGAC
GCAGTTCCTGTGGCGCGTCGAGAGTGCCACGCGCACCTGCTGGCAGGACAAGCTACTGGT
GCTCACCCACGAGGAATCCATCAAGCAGTACAGCTGCGTGGTCAAGCAGAGCTCCACCAC
ATGCTCGACTGGCGGAGGCGAGGGCAGCGCCTGGAGGCTAGACACCAGCATACTGACCTA
CGAAACGCTGGCCAGGAACTTTAGCTGGGCCCAGTGGGATCCCGAGTGCCAGGCTCTTTA
TTACATTCACTTGAAGCCGAAGGCCAAGAGCCTCAGTCTGCTGGACGAGAGGGAGGAGGC
TGGCGAGCAGACAACTCCTACTTTAAGCCCCACGCTCTCCGCCTTTCAGTTTAACGAAAA
ACAGCCAACGGAAACAGTGCTTAATATACCCCTCAATTTGCCAAAGCTGCCCAATGGCTC
CAAAGAGGAATCGCCAAGCTACGATGACGATGCGGTTCCCTTGCGCGTGCACGATAGTTC
GCTAAATCTCATCATACTGGCGGACACCTCGGGCATGTTTTTCGTCTGTCACTACTACCT
GTACCAGCCGATGCAGTCGGAGCAAAGGGATGTGCACTTTGCCTACTCGGTGACTTTGCT
TCACCACGGCTGTGTGGTGCACTGCGTCATGCCCGGTGTGCCGTGGCAAAAGGCCCGTCT
GCTGAGGCCAACATTTGCGCTACACGGCCAGCATCACTTGCTGGTGTCGTCCGCCTTTTT
TGTCCACCTCTTGGACGTGGGACTGCAGCACGAACCGAACTGCCATATCGTGTGTGCAGC
CCACAATCGAAGTCCCGATATCACACAGCTGGTGCCTTTGCGAAAGTGGGGAGCTCTGGC
TTATGATGCGGCTACCTTGGATCTGGTCTCGTTGTCCGTGCCCAAATCCCATTTGATAGA
GGCTTTCCGCAATGACAGTTCGCTGGACAATAGAATCAGCATTATCCACTACTTCCTTTT
CGACTCGAACGATATGGATGTGTTGGCCGAGCTGCTGAACAATATCTTGGAGCGACCACT
CTCCCTGGATACGGTGGCTTTGCTGAAGGAGGCTCTTGTGGCTGGCAGCTATGCGGCTGC
TGTTCGCGGACTACCAGAGGATGCCAAGCCACTGATGCGACTACTGCCATTGACTACTGC
CTTAGCCTCGCGACCAATCCTCGCAAAGGTGGCCGATATAAGCGTGGGTCTCTCTCATGA
AACCCTGCACAATACCAGCATGATGCTGCTCTCGCCACAGCAGCGCCTTTCACCTTATCG
CACGGACATCTGGACTCGCTTATGGGACCTTCTCAACGAGTCAGCCAAGCAGGAGCAGCC
TAGATTCAGTGCTGAGCAGGTGACGGAGAAGTTGATCTTTAGTTTGGCCTGCTACCAGCC
GGAGGCTCTGTCCAGATGCACCACGCCACTTTCGCCAGACACGGGCACCGGTGGATTTGG
TGACTATAGTAGCGGAAGTGCTTTTCCATTCAGCAACGAAGTGCTGCCCTTTATCGAACT
GGAGGGATGCACAGCCAGCAAGCAGGAGCACGTCATTTCTGTGTATCTGCGCGAGCTGAG
CGTTCACCTGGTGAAGCACACGTCAAAGCCCAACACTGGCTTCCGTTGGCTGAAGGAGAC
CTTTTTCGAGCGCTCCCAGGCTCCAGCTCATGTGCATGCGGTGGCCTCGCAGTTCGTTTC
CGCGCAGCTTGAACTCTCGCGGGCTCTTTGCTCTCTGGTTTGTCGTGCTGCAGGCCTAGA
TGCGCGCATGGAGACCTCGAGGGGTTTTCAGTTGATTGACCAAATGGCTGCCAATCAACA
GCACTCTCTGTTTCTAATCCTCGAGCGCTATTGCCTGGCTGTGGAATCAATTGCGTTTCC
CCTGCCCGAGGGTTTCTCCTCGTTCTTCACCTACTTGGGCTATCGTGCGCTGGGCTATGA
TATGTTTCTGCAGTATGTGGAAAATCATGTGTTCGAACTGCAAGTGGATGTGATGAAGGC
CATTGTTTTCGATATTGAAGATTCTCCACTAGGCATTGAGCGGAAGCTATCACTTTTGTC
TGCTCTGCCCAAGCAGCGTGCTCAAAGGTTACTCAAATGCTGGCAGCATCCGGACAGCCT
TATGATCCGCGGACGCGAGCATGCGGCCAACATTCTGTCGGGTCAGCAGCAGGAGGTGTT
GCACCAGCAGCGACCCACGGCCTGCGTGAATCAATCGCGAATAATGGCCGGAGCGATCT
AACTGCCGAAGCCCTTTCGCCACTGGACTCCTTTCTGGACCTGCTGACTGCGAAGGCCAG
TCTAAACGAATTGGACTACAATCTGCTTATTGAAACTACTCTAAGCTCCATCGATCAGCT
GAAACTGGAGGCATGAATTTAATGTTAAGAGTAACTAATGAAGTATTGTGTCAAATTATC
AAGTACTTAGCCAAGGCCAGTTTGCAAATATTCCAAAGATTTGATTTGTCAAATGTATTA
GTTAAGATTCTTCTCGTGCAGCTTTGATTTTGTTAGGGTTCTTCTGTGTGCTTTTAGTA
TTAATTTTCTGTTCCTATAATTTGTGTAACGACTGATACACATTCCAAGTCTGTAATTAT
AAATTATTTATGTTGTTAATTGATGTACCTAAAAAAAA
```

FIG. 2

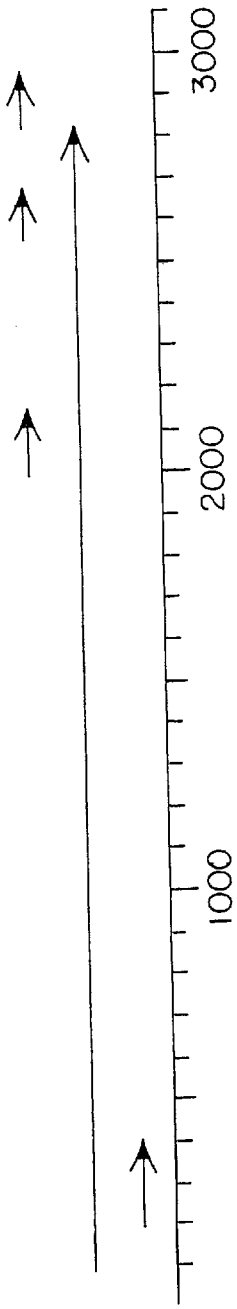

MLRQENLAANFCGLLASQGYKEKANEWRILGQEQDGSLLTSWIFEYADEDQRKETCIGHFHATKKQLRLLWTLDNCREIVQATINSS
VTLLSFVEKTEGKLYQAFVVEVRSSEGGTATPLNSEPSNRQMTQFLWRVESATRTCWQDKLLVLTHEESIKQYSCVVKQSSTTCST
GGGEGSAWRLDTSILTYETLARNFSWAQWDPECQALYYIHLKPKAKSLSLLDEREEAGEQTTPTLSPTLSAFQFNEKQPTETVLNIP
LNLPKLPNGSKEESPSYDDDAVPLRVHDSSLNLIILADTSGMFFVCHYYLYQPMQSEQRDVHFAYSVTLLHHGCVVHCVMPGVPWQK
ARLLRPTFALHGQHHLLVSSAFFVHLLDVGLQHEPNCHIVCAAHNRSPDITQLVPLRKWGALAYDAATLDLVSLSVPKSHLIEAFRN
DSSLDNRISIIHYFLFDSNDMDVLAELLNNILERPLSLDTVALLKEALVAGSYAAAVRGLPEDAKPLMRLLPLTTALASRPILAKVA
DISVGLSHETLHNTSMMLLSPQQRLSPYRTDIWTRLWDLLNESAKQEQPRFSAEQVTEKLIFSLACYQPEALSRCTTPLSPDTGTGG
FGDYSSGSAFPFSNEVLPFIELEGCTASKQEHVISVYLRELSVHLVKHTSKPNTGFRWLKETFFERSQAPAHVHAVASQFVSAQLEL
SRALCSLVCRAAGLDARMETSRGFQLIDQMAANQQHSLFLILERYCLAVESIAFPLPEGFSSFFTYLGYRALGYDMFLQYVENHVFE
LQVDVMKAIVFDIEDSPLGIERKLSLLSALPKQRAQRLLKCWQHPDSLMIRGREHAANILSGQQQEVLHQQRPTACVNQSRNNGRSD
LTAEALSPLDSFLDLLTAKASLNELDYNLLIETTLSSIDQLKLEAZ

ASSOCIATIVE LEARNING AND THE LINOTTE GENE

RELATED APPLICATIONS

This Application claims priority to co-pending U.S. Provisional Application Ser. No. 60/004,845, filed Oct. 5, 1995, the entire teachings of which are incorporated herein by reference.

BACKGROUND OF THE INVENTION

Behavioral analyses of associative learning and memory have revealed a general functional homology among invertebrates and vertebrates (reviewed by Hawkins and Kandel, *Psychol. Rev.* 91:375–391 (1984); DeZazzo and Tully, *Trends Neurosci* 18:212–217 (1995); and Hammer and Menzel, *J. Neurosci* 15:1617–1630 (1995)). Acquisition requires the temporal association of a reinforcing stimulus (US), which naturally elicits a behavioral response, with a conditioned stimulus (CS), which comes to elicit a conditioned response (CR) as a result of the CS-US pairing(s) (Mackintosh, *Conditioning and Associative Learning* (New York: Oxford University Press) (1983)).

A newly acquired experience initially is susceptible to various forms of disruption. With time, however, the new experience becomes resistant to disruption (McGaugh and Herz, *Memory Consolidation* (San Francisco: Calif.: Albion) (1972); Tully et al., *Cold Spring Harbor Symp. Quant. Biol.* 55:203–211 (1990)). This observation has been interpreted to indicate that a labile, short-term memory is "consolidated" into a more stable, long-term memory. This consolidation process depends on protein synthesis (Davis and Squire, *Psych. Bull.* 96:518–559 (1984); Castellucci et al., *J. Neurobiol.* 20:1–9 (1989); Crow and Forrester, *Proc. Natl. Acad. Sci. USA* 87:4490–4494 (1990); Tully et al., *Cell* 79: 35–47 (1994)) and is facilitated by multiple training sessions separated by intervals of rest (Carew et al., *Science* 175:451–454 (1972); Frost et al., *Proc. Natl. Acad. Sci. USA* 82:8266–8269 (1985); Huang and Kandel, *Learn. Mem.* 1:74–82 (1994); Tully et al., *Cell* 79:35–47 (1994)).

This behavioral homology appears to reflect in part an underlying molecular homology. Genetic dissection of olfactory associative learning in fruit flies (reviewed by Davis, *Neuron* 11:1–14 (1993); DeZazzo and Tully, *Trends Neurosci.* 18:212–217 (1995)) and cellular analyses of heterosynaptic facilitation in Aplysia (reviewed by Byrne et al., *In Advances in Second Messenger and Phosphoprotein Research* S. Shenolikar and A. C. Nairn, eds. (New York: Raven Press) pp. 47–107 (1993)) or synaptic long-term potentiation in vertebrates (reviewed by Bliss and Collinrigdge, *Nature* 361:31–39 (1993); Eichenbaum and Otto, *Neurosci.* 16:22–24 (1993)) all have revealed the involvement of the cAMP second messenger system. Temporally paired stimuli induce an increase in cAMP (Wu et al., *Proc. Natl. Acad. Sci. USA* 92:220–224 (1995)) which activates a cAMP-dependent protein kinase (PKA). PKA then serves two functions. In the cytoplasm, activated PKA phosphorylates targets, such as ion channels, thereby modulating synaptic efficacy for minutes to hours (Cowan and Siegel, *J. Neurogenet.* 3:187–201 (1986); Skoulakis et al., *Neuron* 11:197–208 (1993)). Activated PKA also is translocated to the nucleus, where it phosphorylates a cAMP responsive transcription factor, CREB (Dash et al., *Nature* 345:718–721 (1990); Yin et al. *Mol. Cell. Biol.* in press (1995)). Phosphorylated CREB (activator) then initiates a cascade of immediate early genes, including C/EBP (Alberini et al., *Cell* 76:1099–1114 (1994); Bourtchuladze et al., *Cell* 79: 59–68 (1994); Yin et al., *Cell* 79:49–58 (1995)), presumably culminating in a protein synthesis-dependent synaptic growth process (Greenough, *Neurosci.* 7:229–283 (1984); Stewart and Rusakov, *Behav. Brain Res.* 66:21–28 (1995)). This physical change at the synapse may be responsible (at least in part) for more long-lasting modulations of synaptic efficacy and long-term memory.

All the above observations suggest an evolutionarily conserved molecular mechanism involved with the formation of long-term memory: learning-induced activation of the cAMP second messenger system, which terminates in a CREB-mediated transcription factor cascade involved with synaptic growth and function. Although this process may represent a core mechanism common among many species, many other molecules appear to be involved, especially with short-term plasticity (Malinow et al., *Science* 245:862–866 (1989); Abeliovich et al., *Cell* 75:1263–1271 (1993); Mihalek et al., (submitted) (1995)). These observations suggest that the cAMP pathway may be involved only in certain learning tasks and/or that it is more generally necessary but perhaps not sufficient. Indeed, flies homozygous for null mutations of the dunce or rutabaga genes, which encode a cAMP-specific phosphodiesterase and a calcium/ calmodulin-dependent adenylyl cyclase, respectively, nevertheless display significant residual associative learning (Tully and Quinn, *J. Comp. Physiol. A*. 157:263–277 (1985); Tully and Gold, *J. Neurogenet.* 9:55–71 (1993)). Thus, the molecular and behavioral intricacies of learning and memory suggest that additional genes remain to be discovered which may participate in these processes.

SUMMARY OF THE INVENTION

About 2200 P element insertional (transposon-tagged) Drosophila lines were generated and screened for reduced 3 hour memory retention after Pavlovian olfactory learning. The behavior-genetic characterization of two new genes, latheo and linotte, identified from this screen have been described (Boynton and Tully, *Genetics* 131:655–672 (1992); Dura et al., *J. Neurogenet.* 9:1–14 (1993)). Mutant latheo and linotte flies are affected in acquisition of conditioned odor avoidance responses and in rather than memory retention thereafter. Moreover, transposon-tagging these genes allowed their expeditious molecular cloning.

As described herein, the molecular identification of the linotte transcription unit has been achieved. The linotte transcription unit was identified via rescue of the lio$^1$ learning/memory defect by induced expression of a lio$^+$ transgene in adults. The perception of odors or electroshock remained normal when the lio$^+$ transgene was expressed in these lio$^1$ flies. Learning/memory remained normal when the lio$^+$ transgene was expressed in wild-type (lio$^+$) flies.

Only one message is detected throughout the development of wild-type flies, and the level of this transcript is reduced in adult linotte mutants. Sequence analysis of a cDNA clone (SEQ ID NO: 1) corresponding to this mRNA has revealed one 2.7 kb lio$^+$ open reading frame (ORF). Heat-induced expression of a hslio$^+$ transgene three hours before training fully and specifically rescues the learning and memory defects of linotte mutants. These data constitute definitive proof that the correct (linotte) transcription unit has been identified. The deduced amino acid sequence (SEQ ID NO: 2) of this transcript bears no homology to any known protein, indicating that the linotte gene encodes a novel protein involved with associative learning.

In one embodiment of the invention, the novel gene comprises the nucleotide sequence of SEQ ID NO: 1 (the linotte or lio gene). The learning/memory defect caused by disruption of the linotte gene can be specifically and completely rescued by expression of a heat shock promoter lio+ transgene.

The invention also pertains to a protein encoded by a gene of the present invention. In one embodiment, the protein has the amino acid sequence of SEQ ID NO: 2. The invention also pertains to antibodies which bind to the protein encoded by a gene of the present invention.

The invention further pertains to a gene present in cytological region 37 D of the second chromosome which functions in associative learning and/or memory and which hybridizes under standard conditions to the DNA sequence of SEQ ID NO: 1 or the complement of SEQ ID NO:1.

The present invention further provides methods for identifying other genes which function in learning and memory from a variety of organisms, including vertebrates (e.g., mammals and particularly humans), invertebrates (e.g., insects) and microbes (e.g., yeast). Furthermore, comparison of linotte and other learning and/or memory genes and their encoded products provides a way to define key functional features or regions of these genes and gene products. Those features or parts that are conserved between these genes or their gene products are most likely to be functionally important.

The present invention has several applications pertaining to learning and memory. The genetic and molecular characterization of linotte herein can be used to design drugs which mimic or alter the activity of the linotte or other learning and memory genes, and which may, thus, be useful in various therapeutic applications, including learning disabilities, memory defects associated with Alzheimer's disease and other afflictions which are associated with decreased learning and memory.

The complete or partial DNA or amino acid sequence of the linotte gene can also be used as a probe to identify other genes which function in learning and/or memory. The present invention provides methods for identifying other genes which function in learning and memory from a variety of organisms, including vertebrates (e.g., mammals and particularly humans), invertebrates (e.g., insects) and microbes (e.g., yeast).

BRIEF DESCRIPTION OF THE DRAWINGS

FIG. 2 illustrates the 3098 nucleotide complementary DNA sequence of the linotte gene (SEQ ID NO: 1).

FIG. 3A shows conditioned odor avoidance immediately after olfactory learning in wild-type (Can-S), mutant lio$^1$ (lio) and transgenic lio$^1$;hslio$^+$-16 (lio;16) and lio$^1$;hslio$^+$-3 (lio;3) flies in the absence of heat-shock (-hs) or three hours after a 30-minute heat-shock (+hs). FIG. 3B shows memory retention three hours after olfactory learning (three hour retention) in wild-type (Can-S), mutant lio$^1$ (lio) and transgenic lio$^1$;hslio$^+$-16 (lio;16) and lio$^1$;hslio$^+$-3 (lio;3) flies trained in the absence of heat-shock (-hs) or three hours after a 30-minute heat-shock (+hs).

FIG. 4A shows conditioned odor avoidance immediately after olfactory learning in wild-type (Can-S) and transgenic lio$^+$;hslio$^+$-16 (lio+;16) flies in the absence of heat-shock (-hs) or three hours after a 30-minute heat-shock (+hs). FIG. 4B shows memory retention three hours after olfactory learning in wild-type (Can-S) and transgenic lio$^+$;hslio$^+$-16 (lio+;16) flies trained in the absence of heat-shock (-hs) or three hours after a 30-minute heat-shock (+hs).

FIGS. 5A and 5B show the open reading frame (ORF) and deduced amino acid sequence of the linotte gene. FIG. 5A depicts ORF maps of each reading frame of the lio$^+$ sense strand. All ORFs initiating with an AUG and longer than 100 nucleotides (nt) are indicated with arrows above a linear representation of the lio$^+$ cDNA. FIG. 5B depicts the deduced 916 amino acid sequence (SEQ ID NO: 2) of the 2748 nt lio$^+$ ORF.

DETAILED DESCRIPTION OF THE INVENTION

The invention described herein pertains to a novel gene, comprising the DNA sequence of SEQ ID NO: 1, present in cytological region 37 D of the second chromosome and which functions in associative learning and/or memory. Disruption of the gene, such as by P element transposon-tagged insertion, results in decreased associative learning and/or memory.

The teachings of references cited herein are incorporated herein by reference in their entirety. Terms used herein are intended to have their art-recognized meanings unless otherwise indicated. As used herein, the term "disruption" of a gene is intended to mean any alteration of the nucleotide sequence of the gene or the amino acid sequence of the encoded protein from the wild type, including a frameshift, insertion or deletion.

Figure 4A:
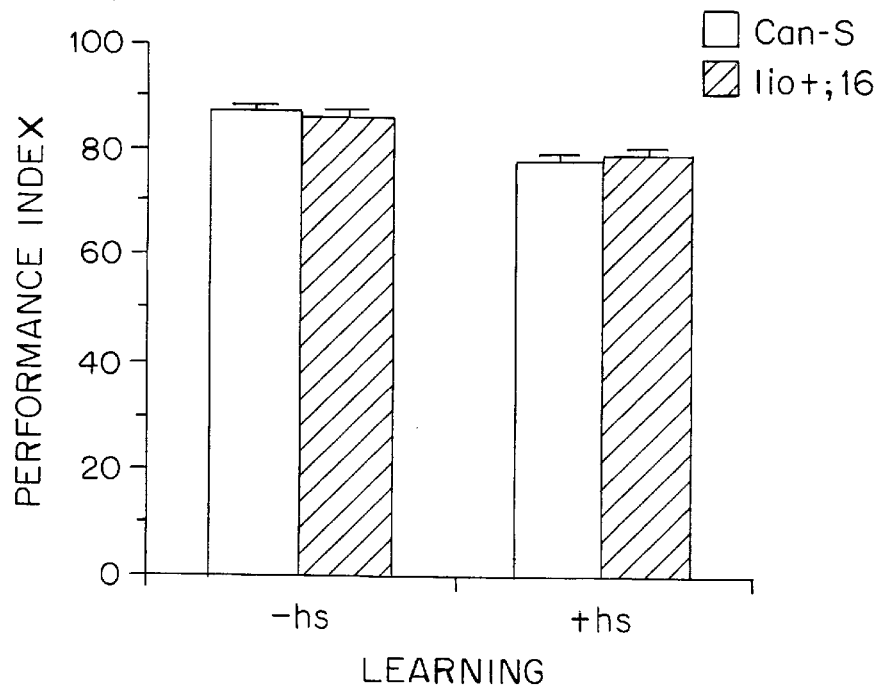
FIGS. 4A and 4B are graphic representations of the effect on learning and memory in lio$^+$ (wild-type) flies of heat shock-induced expression of the hslio$^+$ transgene.
Figure 4B:
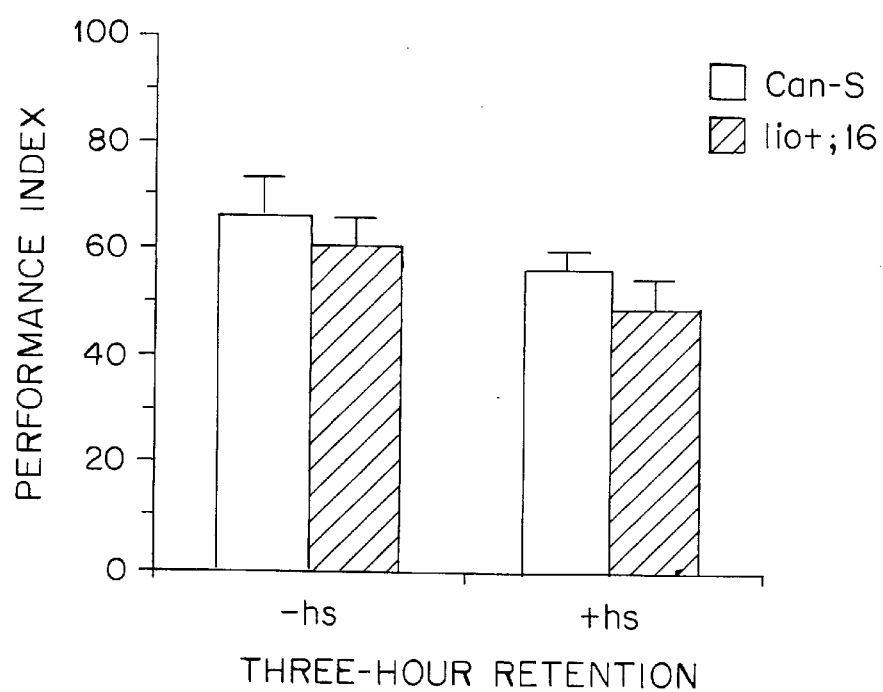

Two transgenic lines (lio$^1$;hslio$^+$-16 and lio$^1$;hslio$^+$-3), carrying independently isolated genomic insertions of a heat shock promoter-linotte (hslio$^+$) transgene, showed normal olfactory learning and memory after expression of the transgene was induced by heat shock in adults (FIGS. 4A and 4B). This rescue effect is behaviorally specific, since induced expression of the hslio$^+$ transgene did not affect the flies' task-relevant abilities to sense the odors (olfactory acuity) or electroshock (shock reactivity) used in the Pavlovian experiments (Table 1; cf. Dura et al., *J. Neurogenet* 9:1–14 (1993)).

It should be noted that any appropriate promoter can be used to drive the expression of the hslio$^+$ transgene; the appropriateness of the promoter will depend on the environment and specifically desired expression. For instance, in some cases it will be desirable to create a lio+ transgene driven by an inducible promoter such as the heat shock or metalothionein promoters. In other situations it will be desirable to drive expression of the lio transcript using a constitutive promoter. For instance, when expressing the Lio protein in cell culture, the desired promoter can vary depending upon the purpose of the protein expression.

Complete rescue of the $lio^1$ learning/memory defect in induced $hslio^+$ flies indicated that ectopic expression of the $lio^+$ transgene does not produce any deleterious effects on conditioned olfactory behavior. The other extreme also was considered; that is, that (ectopic) expression of the $hslio^+$ transgene might produce a general enhancement, thereby improving learning/memory in $lio^1$ mutants nonspecifically. This possibility was tested by inducing overexpression of the $hslio^+$ transgene in $lio^+$ (wild-type) flies, rather than in $lio^1$ mutants. In such transgenic $lio^+;hslio^+$-16 flies, learning/memory was normal. Thus, induced expression of the $hslio^+$ transgene did not produce a general enhancement of learning or memory. Consequently, it can be concluded that the deleterious effects on learning and memory of the $lio^1$ mutation specifically were rescued by induction of the $hslio^+$ transgene.

In the absence of heat shock, transgenic $lio^1;hslio^+$ flies show learning/memory deficits similar to those of $lio^1$ mutants (FIGS. 4A and 4B), and expression of the transgene is not detected in adult heads. Conditioned odor avoidance after olfactory learning was quantified as a mean Performance Index (PI) 241±SEM. If no flies learn to avoid the shock-paired odor, then PI=0; if all flies learn, then PI=100. N=6 PIs per group.

In contrast, three hours after heat shock, learning and memory are rescued completely, and expression of the transgene in adult heads is high. Combined with data from the developmental Northern blot, which revealed undetectable levels of the linotte transcript throughout larval development, and from histological studies of mutant adult brain, which revealed no structural abnormalities in mushroom bodies or central complex, these results indicate clearly that the learning/memory deficit of $lio^1$ mutants does not derive secondarily from developmental abnormalities. Instead, the linotte gene appears to function more acutely during adult associative learning (cf. Ewer et al., Nature 333:82–84 (1988)). This inducible, complete and behaviorally-and molecularly-specific rescue of the linotte learning/memory deficit constitutes definitive proof that the linotte transcription unit was correctly cloned and identified.

A high level of $lio^+$ expression in early embryos followed by much lower levels in late embryos suggests that $lio^+$ initially is maternally derived. Appreciable levels of expression are not observed again until the pupal and adult stages. PolyA+ RNA was extracted from wild-type (Canton-S) early embryos (0–4 hour embryo), late embryos (>16 hour embryo), first, second or third instar larvae, pupa, adult head and adult body, electrophoresed on a 1% denaturing agarose gel, transferred to a charged nylon membrane and probed with $^{32}$P-radiolabeled $lio^+$ (3.1 kb) cDNA (L) and rp49 (R) as described above. When comparing the temporal patterns of expression between the linotte transcript and the enhancer-trap reporter gene encoded within the $lio^1$ P element insertion, an apparent discrepancy exists. The former cannot be detected in any larval stage, while the latter is expressed at high levels in the lateral brain hemispheres of third-instar larvae (data not shown). Recent identification of the derailed (drl) gene, however, has revealed a more specific resolution to this discrepancy for $lio^1$ (Callahan et al., Nature (in press) (1995)).

Figure 1:
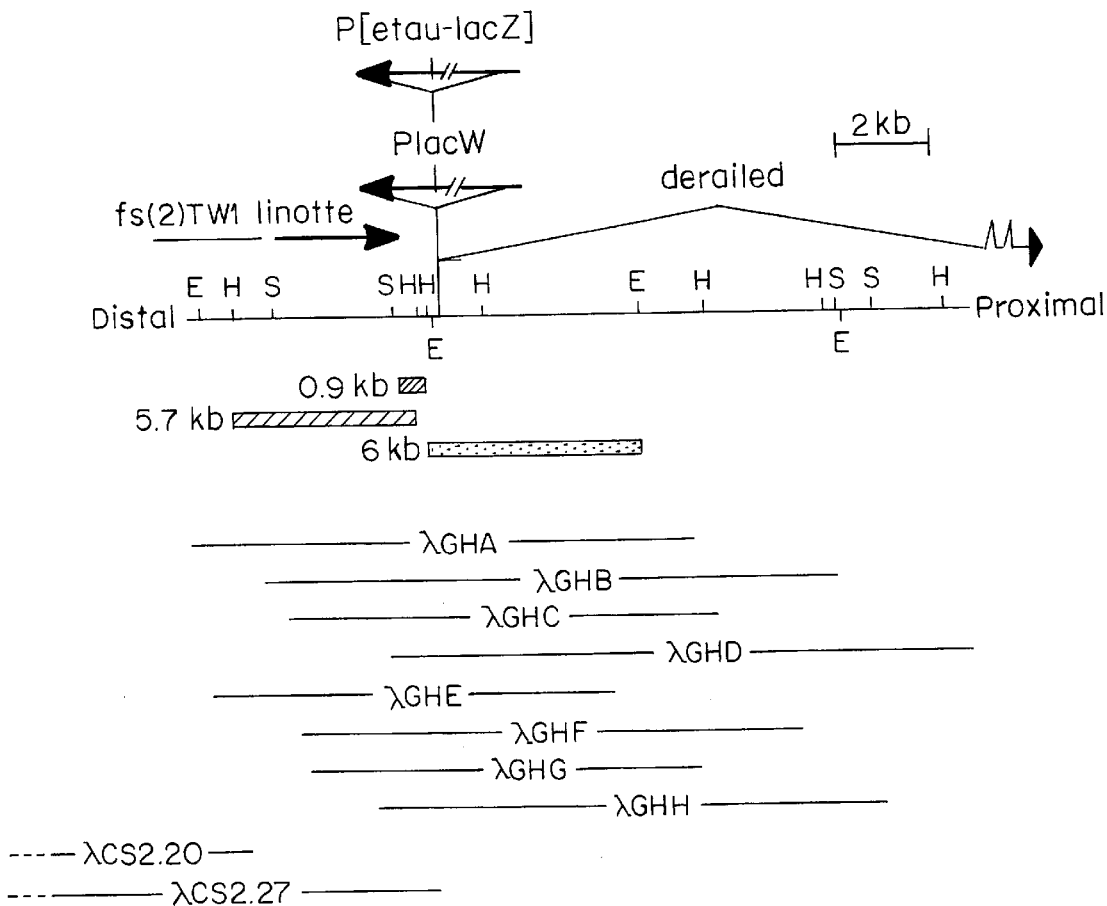
FIG. 1 depicts a schematic nap of genomic DNA in cytological region 37 D of the second chromosome, which contains the linotte gene. The restriction fragment map shows sites for EcoRI (E), HindIII (H) and Sac II (S). The PlacW P element transposon, which causes the lio$^1$ mutation, is depicted as a grey arrow indicating the transcriptional orientation of the lacZ reporter gene; its point of insertion in the genome is marked by a descending line. The linotte transcript is indicated by a black arrow. The P[etau-lacZ] P element, which causes the derailed mutation, is represented by a grey arrow indicating the transcriptional orientation of the etau-lacZ reporter gene. The 5.7 kb HindIII—HindIII, the 6 kb EcoRI-EcoRI and the 0.9 kb SacII-HindIII genomic restriction fragments, which were used to probe cDNA or genomic libraries, are represented by boxes below the restriction map. Genomic phage clones (λ) identified either with the 0.9 kb SacII-HindIII restriction fragment (λGHA-λGHH) or from the Ddc project (λCS2.20 and λCS2.27) are indicated as lines below.

DNA sequence comparison has shown that the identified $lio^1$ P element is inserted six base pairs distal to the independently isolated P element insertion in drl (FIG. 1). The derailed transcript lies proximal (right), and the fs (2)TWl transcript lies distal (left), to the linotte transcript. Consistent with this finding, the embryonic CNS patterns of reporter gene expression for both P element insertions correspond to the expression pattern of the drl gene itself (C. Cahallan and J. Thomas, personal comm.). Moreover, the derailed transcript is expressed throughout larval development but is undetectable in adult flies. The latter result is consistent with our Northern blot analysis of adult head RNA, in which a genomic DNA fragment proximal to the $lio^1$ P element insertion (and including at least some of the derailed exonic sequence) failed to detect any transcript.

These data indicate that the $lio^1$ P element affects the level of expression of the linotte transcript in adult flies—thereby producing a learning/memory deficit—even though it is inserted in or near the 5' end of the drl transcription unit. It is not yet known whether the $lio^1$ P element insertion also produces the derailed mutant phenotype, axonal misguidance in a subset of neurons during development of the nervous system in embryos (Callahan et al., Nature (in press) (1995)). Nevertheless, these potential pleiotropic defects do not prevent complete rescue of the $lio^1$ learning/memory defect after the $hslio^+$ transgene is induced in adults.

To date, RNA in situ hybridization studies using linotte RNA probes have failed to produce any detectable signal in adult brain sections. Immunocytochemical studies using antibodies raised against the linotte gene product, however, may reveal its cellular localization.

The linotte gene originally was isolated in a behavioral screen for P element insertional mutations that disrupted 3-hour retention after Pavlovian olfactory learning. To date, behavioral characterization of 2200 hundred P element Lines has yielded four new learning/memory genes, linotte[1], latheo$^{Pl}$, nalyot card golovan (Boynton and Tully, Genetics 131:655–672 (1992) Dura et al., J. Neurogenet 9:1–14 (1993) and T. Tully unpublished data). The transposon-tagging method was chosen for two reasons particularly relevant to behavioral phenotypes. First, the P element mutator contained a selectable eye-color marker, which yielded morphologically tagged behavioral mutants. Consequently, subsequent genetic experiments were greatly facilitated. Second, the P element mutator represented a molecular tag with which to clone genomic DNA flanking the insertion site. This approached gained access to genomic DNA in the region of the P element insertion but was not designed to identify unambiguously the transcription unit specifically responsible for the learning/memory deficit.

The particular set of molecular-genetic, histological and behavioral data derived from linotte cloning has yielded important information. Insertion of the P element into a transcription unit is not sufficient evidence to conclude that the particular transcript is involved with the behavioral defect. Correspondence between patterns of expression of an enhancer-trap reporter gene (contained within the transposon) and of a nearby transcript also does not constitute sufficient evidence to conclude that the particular transcript is involved with the behavioral phenotype. The only evidence sufficient to draw such a conclusion is rescue of the mutant phenotype by expression of a (wild-type) transgenic transcript, along with controls for behavioral and molecular specificity. Although the issue of behavioral specificity seems trivial in light of the complete rescue of mutant $lio^1$ learning/memory, it becomes quite relevant when only partial rescue of a learning/memory defect is observed, as recently has been reported for the dunce gene (Dauwalder and Davis, *J. Neurosci.* 15:3490–3499 (1995)).

This singular criterion is particularly relevant for P element-derived mutations, since these large foreign pieces of DNA are likely to disrupt the expression of several nearby genes. Phenotypic rescue in transgenic flies is sufficient, as well, for ethylmethane sulfonate (EMS)-induced mutations, which tend to produce more restricted (even single-nucleotide) molecular lesions. When multiple, independently derived mutant alleles are available, however, a second approach can be used to identify the relevant transcription unit; molecular lesions corresponding to each of several mutations can be shown to reside within the same transcription unit (e.g., bithorax; Bender et al., *Science* 221:23–29 (1983)).

Of particular interest is the observation that the linotte gene encodes a previously unknown protein. Future studies will reveal the biological function(s) of this new gene. Given the frequency with which learning/memory mutants were identified from our screen (1 mutant per 550 P element lines) and the speed with which the correct transcript was identified for linotte, this approach in Drosophila appears particularly expeditious. With substantial molecular and behavioral homology for associative learning and memory processes already documented among fruit flies, bees, mollusks and vertebrates (see DeZazzo and Tully, *Trends Neurosci.* 18:212–217 (1995) for a review), trans-species homologs of the linotte gene are anticipated.

This evidence suggests that there may be a human equivalent of the linotte gene; using linotte, other associative learning/memory genes from a variety of organisms can be obtained, for example by hybridization procedures known in the art. The sequences of these related genes and their encoded products can be compared, for instance, using computer-based analysis, to determine their similarities. Structural comparisons, for example, would indicate those regions or features of the genes or encoded products which are likely to be functionally similar and important. Such information can be used to design drugs which mimic or alter the activity of the linotte or other learning and memory genes, and which may, thus, be useful in the various therapeutic applications, including learning disabilities, memory defects associated with Alzheimer's disease and other afflictions which age associated with decreased learning and memory.

In addition, comparison of equivalent genes and their encoded products, as well as mutational analysis, is expected to indicate key functional features or regions of the genes or gene products. The learning and memory genes and their gene products are further useful for developing and identifying agents which affect the activity of the described associative learning genes. These agents may be useful for altering (increasing or decreasing) the occurrence of learning and/or memory defects in an organism, and thus, altering the learning ability and/or memory capacity of the organism.

The invention will be further illustrated by the following non-limiting examples:

EXAMPLES

Plasmid Rescue and cDNA Cloning

Genomic sequences flanking the linotte P-element were cloned by plasmid rescue using standard techniques (Sambrook et al., *Molecular cloning*: A Laboratory Manual, Cold Spring Harbor Laboratory (1989); Wilson et al., *Genes Dev.* 3:1301–1313 (1989)). Briefly, linotte genomic DNA was digested with SacI, followed by ligation to form a rescue plasmid, which was propagated in *E. coli* LE392. The rescue fragment then was $^{32}$P-radiolabeled by random priming and used to screen 3×10$^7$ phage plaques from a Drosophila genomic bacteriophage λ-DASH library (Sambrook et al., *Molecular cloning: A Laboratory Manual*, Cold Spring Harbor Laboratory (1989)). The 5.7 kb Hind III λ genomic fragment (FIG. 1) was subcloned into the plasmid vector pBS-KS+, radiolabeled and used to probe a Northern blot of adult whole fly polyA+ RNA and a λgt11 Drosophila adult head cDNA library. A 6 kb EcoRI fragment (FIG. 1) corresponding to the sequences distal to the lio$^1$ P-element was subcloned into the plasmid vector pBS-KS+, radiolabeled and used to probe a Northern blot of adult head polyA+ RNA. A 3.1 kb EcoRI lio cDNA fragment was excised from the λ page and subcloned into the plasmid vector pBS-KS+. This is 3.1 kb insert (containing the 2.7 kb ORF) was cloned into the EcoRI (polylinker) site of the transformation vector CaSpeR-has, which contains a white$^+$ minigene as a selectable marker and P-element sequences to facilitate insertion into the genomic DNA (Pirrotta, *Biotechn.* 10:437–456 (1988)). This transgene construct was designated hslio$^+$.

Fly Stocks

The genetic background of w;lio$^1$ mutants was equilibrated with that of the wild-type (Canton-S) strain by repeatedly backcrossing heterozygous w/w;lio$^1$/+females (which carried the mw$^+$ eye-color marker) to w(CS10) males for more than five generations. The w(CS10) strain was derived by backcrossing w$^{1118}$ flies to wild-type (Canton-S) flies for 10 generations (Dura et al., *J. Neurogenet.* 9:1–14 (1993)); the w(isoCJ1) strain was derived from w(CS10) and carries isogenic X, 2nd and 3rd chromosomes (Yin et al., *Cell* 79:49–58 (1994); Yin et al., *Cell* 81:107–115 (1995a)). Homozygous w;lio$^1$ flies (hereafter referred to as lio$^1$) were bred a few months before behavioral experiments. For histological experiments, lio$^1$ homozygotes or another "wild-type" PlacW transposant strain, E$_j$4(TP) which showed normal olfactory acuity, shock reactivity and olfactory learning, were cooled and then crossed to flies carrying the second chromosome deletion Df(2L)VA12 (hereafter referred to as Df) and the CyO second chromosome balancer. Straight-winged flies from each cross, lio$^1$ mutants and E$_j$4(TP) flies then were processed together and decoded after the planimetric analysis (see below). To generate transgenic flies, approximately 3000 w(isoCJ1) embryos were dechorionated with 40% aqueous bleach for 60 seconds, rinsed in water, desiccated at 18° C. and 60% R.H. for approximately 20 minutes, aligned on acetate-based double-sided tape (3M type 415, 3M, St. Paul, Minn.) and coinjected with hslio$^+$ and with the transposase-source plasmid pUChspD2-3wc (Rubin and Spradling, *Science* 218:348–353 (1982); Spradling and Rubin, *Science* 218:341–347 (1982)). Approximately 200 G$_0$ flies were recovered and mated to w(isoCJ1), from which 18 independent, fertile transformant lines were established. These transgenic lines were designated lio$^+$;hslio$^+$-X. Flies from four transgenic lines, carrying hslio$^+$ insertions in the third chromosome (lio$^+$;hslio$^+$-16,lio$^+$;hslio$^+$-3,lio$^+$;hslio$^+$-21 and lio$^+$;hslio$^+$-1), were crossed with lio$^1$ mutants to recover heterozygous lio$^+$/+; hslio$^+$/+progeny, which were identified by eye color. These heterozygotes then were mated to a "cantonized" CyO/Sp;TM6B/Sb double balancer strain to yield lio$^1$/+; hsli$^+$/progeny, which were identified by eye color. These heterozygotes then were mated to a "cantonized" CyO/Sp;TM6B/Sb double balancer strain to yield lio$^1$/CyO;hslio$^+$/TM6B progeny. Intermating of these flies yielded four lines homozygous for the lio$^1$ mutation on the second chromosome and for the hslio$^+$ transgene on the third chromosome. These transgenic lines were designated lio$^1$;hslio$^+$-X.

RNA Isolation and Northern Blotting

Flies were collected and sacrificed immediately by flash-freezing in liquid nitrogen. Where applicable, Drosophila adult head and body mRNA was made by vigorously shaking frozen flies and separating the frozen heads and bodies by sifting over dry ice. The frozen parts were pulverized in a mortar on dry ice and then extracted using the acidic guanidinium isothiocyanate method (Chomczynski and Sacchi, *Analytical Biochemistry* 162:156–159 (1987)). PolyA+RNA subsequently was selected by oligo(dT)$^+$ chromatography (Chirgwin et al., *Biochemistry* 18:5294 (1979)). The polyA+ RNA then was electrophoresed on a 1% formaldehyde agarose gel, transferred to a charged nylon membrane and probed with the radiolabeled 3.1 kb cDNA fragment or with a fragment from the Drosophila ribosomal protein gene 49 (rp49) (Church and Gilbert, *Proc. Natl. Acada. Sci. USA* 81:1991 (1984); O'Connell and Rosbash, *Nucl. Acids Res.* 12:5495–5513 (1984)). Two Northern blots were generated, each containing polyA+ RNA from wild-type flies and lio$^1$ mutants. Bands intensities were determined by phosphorimage analysis (Fuji Photo Film Co.). Intensity of the lio$^+$ transcript was normalized to that of rp49 within a given lane (wild-type or mutant). Levels of expression of the lio$^+$ transcript in lio$^1$ mutants then were expressed as percentages of the levels of expression of the lio$^+$ transcripts in wild-type flies in each corresponding Northern blot. Finally, these two percentages of expression were averaged.

Expression of the linotte (lio$^+$) transcript is reduced in lio$^1$ mutants and is not affected by heat shock, while expression of the hslio$^+$ transgene is induced by heat shock (data not shown). In the absence of heat shock, twice as much lio$^+$ transcript is expressed in wild-type (Canton-S) adult heads as in mutant lio$^1$ heads or in transgenic lio$^1$;hslio$^+$-16 heads, while expression of the hslio$^+$ transgene was not detected. Three hours after heat shock, when flies were subjected to olfactory learning, expression of the lio$^+$ transcript was unchanged in wild type, mutant lio$^1$ or transgenic lio$^1$;hslio$^+$-16 flies. In contrast, the hslio$^+$ transgene was expressed at a high level. Six hours after heat-shock, when 3-hour memory after olfactory learning was assayed, expression of the hslio$^+$ transgene was greatly diminished. PolyA+RNA was extracted from wild-type (Can-S), lio$^1$ (lio) and lio$^1$;hslio$^+$-16 (lio;16) adult heads, electrophoresed on a 1% denaturing agarose gel, transferred to a charged nylon membrane and probed with $^{32}$P-radiolabeled lio$^+$ (3.1 kb) cDNA. To quantify relative amounts of RNA loaded into each lane, this Northern blot was reprobed with a $^{32}$P-radiolabeled DNA fragment from the ribosomal protein 49 (rp49) gene. Radiolabeled signals finally were quantified with a phosphorimager, and signal intensities of hands hybridizing with the lio$^+$ probe were normalized using rp49 signal intensities from each corresponding lane.

Histology

To quantify the neuropilar volumes of mushroom bodies and central complex, paraffin sections of lio$^1$, lio$^+$[E$_j$4(TP)],lio$^1$/Df and lio$^+$/Df flies were prepared as by Ashburner (*Drosophila—A Laboratory Manual* (Plainview N.Y.: Cold Spring Harbor Laboratory Pres, 1989) with a few modifications: Heads were first incubated in 1:1 (methylbenzoate:low melting paraffin), followed by six 30 minute incubations with pure paraffin. Seven μm frontal sections were inspected visually at 400× magnification. The volumes of mushroom body or central complex neuropil then were quantified via planimetric analysis using an MTI CCD 725 camera connected to a Screen Machine Classic Videoboard (FAST electronic GhbH, Munich, Germany) in an MS-DOS PC with custom software developed by R. Wolf and M. Heisenberg (Heisenberg 1995). The operator traced the outlines of mushroom body calyces and the central complex (including the noduli and fan-shaped body) through serial sections while blind to genotype.

Xgal Staining of Tissues

Embryos were dechorionated, fixed in 3.7% formaldehyde in PBS and X-gal stained as described (Ashburner, *Drosophila. A Laboratory Manual*, Plainview N.Y.: cold Spring Harbor Laboratory Press (1989)). Larval CNSs were dissected in Ringer's solution, fixed in 30% glutaraldehyde and X-gal stained as described (Ashburner, *Drosophila. A Laboratory Manual*, Plainview N.Y.: cold Spring Harbor Laboratory Press (1989)) for one hour at 37° C. Adult heads were imbedded in OCT, sectioned in a cryostat, fixed in 1% glutaraldehyde/PBS, X-gal stained and mounted as described by Han et al. *Neuron* 9:619–627 (1992)).

Behavioral Analysis of Transgenic Flies

Preparation of flies

Before behavioral assays, approximately 600 1-to-2-day old flies were placed in a foam-plugged ½ pint glass bottle with standard food and a wad of paper towel. These flies were stored overnight at 25° C. and 50% relative humidity. The next morning, groups that were destined for the heat-shock treatment (37° C. for 30-minutes) were transferred to foam-plugged, 15×85 mm glass vials with a 10×20 mm strip of Whatman 3M filter paper. The vials were placed in a water bath, ensuring that the fly chamber was completely submerged. After this heat shock regimen, the flies were transferred to a standard food vial where they recovered for three hours at 25° C. and 50% relative humidity, at which time behavioral assays commenced.

Pavlovian Learning/memory

To analyze associative learning, the Pavlovian conditioning procedure of Tully and Quinn (*J. Comp. Physiol. A*. 157:263–277 (1985)) was used. Briefly, groups of about 100 flies were trained in a tube with an internal electrifiable grid. The tube was sequentially ventilated with two odorants, 3-octanol (OCT;ICN Biochemical, Aurora Ohio) and 4-methylcyclohexanol (MCH; Fluka Chemie AG, Buchs CH) at concentrations equally aversive to untrained flies. The flies were exposed for 60 seconds to OCT (CS+), while being given twelve 1.5-s pulses of 60 V (DC) electroshock every 5 seconds, followed by a 45-second rest period. The flies then were exposed for 60 seconds to MCH (CS−) without any electroshock, which again was followed with a 45-s rest interval. To test for learning, the trained flies were tapped into a T-maze immediately after this discriminative conditioning procedure. Air laced with the CS+ or CS− was drawn through each of the two respective arms of the T-maze, and the flies were allowed 120 seconds to migrate into either t-maze arm. At the end of this test trial, the flies were trapped in the T-maze arms, anesthetized and counted. For one complete experiment, this training/testing procedure was repeated with a second group of flies using the reciprocal odor combination (MCH as CS+ and OCT as CS−). The total numbers of flies in the T maze arms then were used to calculate the proportions "correctly avoiding" the CS+ (they were in the CS− T-maze arm), and the two values from reciprocal experiments were averaged. Finally, a performance index (PI) for one complete experiment was calculated by normalizing tile average proportion "correctly avoiding." PIs could range from 0 (a 50:50 distribution in the T-maze; no learning) to 100 (all flies avoid the CS+). To measure 3-hour retention, trained flies were transferred to a food vial, where they were stored at 25° C. during the retention interval. Seventy-five seconds before the test trial, flies were transferred to the choice point of the T-maze and tested as described above.

Olfactory Acuity

The flies' ability to smell the odorants used during Pavlovian conditioning experiments was quantified by exposing groups of untrained flies for 120-seconds to odor vs. air in the T-maze (see Boynton and Tully, *Genetics* 131:655–672 (1992)). Typically, two odor concentrations were used: undiluted, as in the Pavlovian experiments, and a 100-fold dilution. Performance indices (PIs) were calculated as above but for each group separately. To control for "side bias," equal numbers of groups were assayed with odor in the right arm, or odor in the left arm, of the T-maze.

Shock Reactivity

The flies' ability to sense the electroshock used during Pavlovian conditioning experiments was quantified by introducing groups of untrained flies into a testing T-maze where both arms contain electrifiable grids. One of the two arms were electrified as above, and the flies chose between shock vs. no shock for 120 seconds (see Luo et al. *Neuron* 9:595–605 (1992); the primary reference to this method was incorrectly stated as Dura et al. *J. Neurogenet.* 9:1–14 (1993) in Tully et al., *Cell* 79:35–47 (194); Yin et al., *Cell* 79:49–58 (1994); Yin et al., *Cell* 81:107–115 (1995)). Typically, two shock voltages were used: 60 V, as in the Pavlovian experiments, and 20 V. Performance indices (PIs) were calculated as in olfactory acuity experiments.

Statistical Analysis of Behavioral Data

PIs are distributed normally (Tully and Gold, *J. Neutrogenet.* 9:55–71 (1993), so untransformed data were analyzed parametrically with the Macintosh software package JMP 3.1 (SAS Institute, Inc.). All pairwise comparisons were planned. To maintain an experiment wise error rate of $\beta=0.05$, the critical P values were adjusted accordingly (Sokal and Rohlf, *Biometry* (New York, Freeman 1981)); Audesirik and Audesirik, *NeuroToxicology* 10:659–670 (1989)) and are listed below for each experiment. All behavioral experiments were performed in a balanced fashion, with N=2 PIs collected per day per group (genotype ±hs). In these experiments, the experimenter was blind to genotype.

Learning in Wild-type (Canton-S), Mutant ($lio^1$) and Transgenic ($lio^1;hslio^+$-16 or $lio^1;hslio^+$-3) Flies With and Without Heat Shock PIs from four genotypes (wild type, liol,$lio^1;hslio^+$-16 or $lio^1;hslio^+$-3) and two heat shock regimens (–hs or +hs) were subjected to a two-way ANOVA with geno ($F_{(3, 72)}$=71.30, P<0.001) and heat shock regimen ($F_{(1, 72)}$=17.74, P0.001) as main effects and gene x heat ($F_{(3, 72)}$=21.68, P0.001) as an interaction term. In the absence of heat-shock, learning in $lio^1$ mutants was significantly lower than in wild-type flies (P<0.001), while learning in transgenic $lio^1;hslio^+$-16 and $lio^1;hslio^+$-3 flies was similar to that in $lio^1$ mutants (P=0.015 and P=0.87, respectively). When trained three hours after heat-shock, learning in $lio^1$ mutants still was significantly lower than that in wild-type flies (P<0.001), but learning in transgenic $lio^1;hslio^+$-16 and $lio^1;hslio^+$-3 flies was significantly improved (P<0.001 for each) and did not differ from wild type flies (P=0.071 and P=0.22, respectively). In contrast to this clear effect of heat shock on learning in transgenic flies, heat shock had no effect on learning in wild type flies (P=0.006) or in $lio^1$ mutants (P=0.084). The ten planned comparisons were deemed significant if $P\leq 0.005$.

Three-hour Retention in Wild-type (Canton-S), Mutant ($lio^1$) and Transgenic ($lio^1;hslio^+$-16 or $lio^1;hslio^+$-3) Flies With or Without Heat Shock PIs from four genotypes (wild-type, $lio^1$, $lio^1;hslio^+$-16 or $lio^1;hslio^+$-3) and two heat shock regimens (–hs or +hs) were subjected to a two-way ANOVA with geno ($F_{(3, 72)}$=20.54, P<0.00) and heat shock regimen ($F_{(1, 72)}$=20.49, P<0.001) as main effects and geno x heat ($F_{(3, 72)}$=7.67, P<0.001) as an interaction term. The ten planned comparisons were deemed significant if $P\leq 0.005$. As was true for learning, three-hour retention in $lio^1$ mutants was significantly lower than in wild-type flies (P<0.001) in the absence of heat-shock, while learning in transgenic $lio^1;hslio^+$-16 and $lio^1;hslio^+$-3 flies was similar to that in $lio^1$ mutants (P=0.76 and P=0.91, respectively). When trained three hours after heat-shock, three-hour retention in transgenic $lio^1;hslio^+$-16 and $lio^1;hslio^+$-3 flies was significantly improved (P<0.001 for each) and did not differ from wild-type flies (P=0.67 and P=0.69, respectively). In contrast to this clear effect of heat shock on three-hour retention in transgenic flies, heat shock had no effect on three-hour retention in wild-type flies (P=0.763) or in $lio^1$ mutants (P=0.93).

Olfactory Acuity in Wild-type (Canton-S) and Transgenic ($lio^1;hslio^+$-16) Flies PIs from two genotypes (wild-type of $lio^1;hslio^+$-16), four odor/concentration groups, (OCT $10^{-2}$; OCT $10^0$; MCH $10^{-2}$ or MCH $10^0$) and two heat shock regimens (–hs or +hs) were subjected to a three-way ANOVA with genotype ($F_{(1, 128)}$=0.29, P=0.59), odor ($F_{(3, 128)}$+61.76, P<0.001) and heat shock regimen ($F_{(1, 128)}$=33.33, P<0.001) as main effects, with geno x odor ($F_{(3, 128)}$+1.79, P=0.15), geno x heat ($F_{(1, 128)}$=0.04, P=0.84) and odor X heat ($F_{(3, 128)}$=0.15, P=0.9) as two-way interaction terms and with gene x odor x heat ($F_{(3, 128)}$+0.15, P=0.93) as the three-way interaction term. The twelve planned comparisons were judged significant if $P\leq 0.004$ and are summarized in Table 1.

Shock Reactivity in Wild-type (Canton-S) and Transgenic ($lio^1;hslio^+$-16) Flies PIs from two genotypes (wild-type or $lio^1;hslio^+$-16), two voltages (20 V or 60 V) and two heat shock regimens (–hs or +hs) were subjected to a three-way ANOVA with geno ($F_{(1, 64)}$=0.57, P=0.45), volt ($F_{(1, 64)}$=97.47, P<0.001) and heat shock regimen ($F_{(1, 64)}$=0.14, P=071) as main effects, with geno x volt ($F_{(1, 64)}$=0.63, P=0.43), geno x heat ($F_{(1,64)}$=0.21, P=0.65) and volt x heat ($F_{(1, 64)}$=2.81, P=0.10) as two-way interaction terms and with geno x volt x heat ($F_{(1, 64)}$=0.63, P=0.43) as the three-way interaction term. The six planned comparisons were judged significant if $P\leq 0.01$ and are summarized in Table 1.

Learning in Wild-type (Canton-S) and Transgenic ($lio^+;hslio^+$-16) Flies With or Without Heat Shock PIs from two genotypes (wild-type or $lio^+;hslio^+$-16) and two heat shock regimens (–hs or +hs) were subjected to a two-way ANOVA with genotype ($F_{(1, 20)}$=0.02, P=0.89) and heat shock regimen ($F_{(1, 20)}$=36.04, P<0.001) as main effects and geno x heat ($F_{(1, 20)}$=0.39, P=0.54) as an interaction term. Conditioned odor avoidance after olfactory learning was quantified as described above. N=6 PIs per group. The two planned comparisons were deemed significant if $P\leq 0.05$, and results are summarized in FIG. 4A. Learning in transgenic flies did not differ significantly from wild-type flies in the absence of (P=0.60), or when trained three hours after (P=0.73), heat-shock.

Three-hour Retention in Wild-type (Canton S) and Transgenic ($lio^+;hslio^+$-16) Flies With or Without Heat Shock PIs from two genotypes (wild-type or lio$^+$;hslio$^+$-16) and two heat shock regimens (–hs or +hs) were subjected to a two-way ANOVA with geno ($F_{(1, 20)}$=1.27, P=0.27) and heat shock regimen ($F_{(1, 20)}$=3.37, P=0.08) as main effects and geno x heat ($F_{(1, 20)}$=0.01, P=0.93) as an interaction term. The two planned comparisons were deemed significant if P<0.05 and are summarized in FIG. 4B. As was true for learning, three-hour retention in transgenic flies did not differ significantly from wild-type flies in the absence of (P=0.47), or when trained three hours after (P=0.40), heat-shock.

Statistical Analysis of Histological Data

Figure 6:
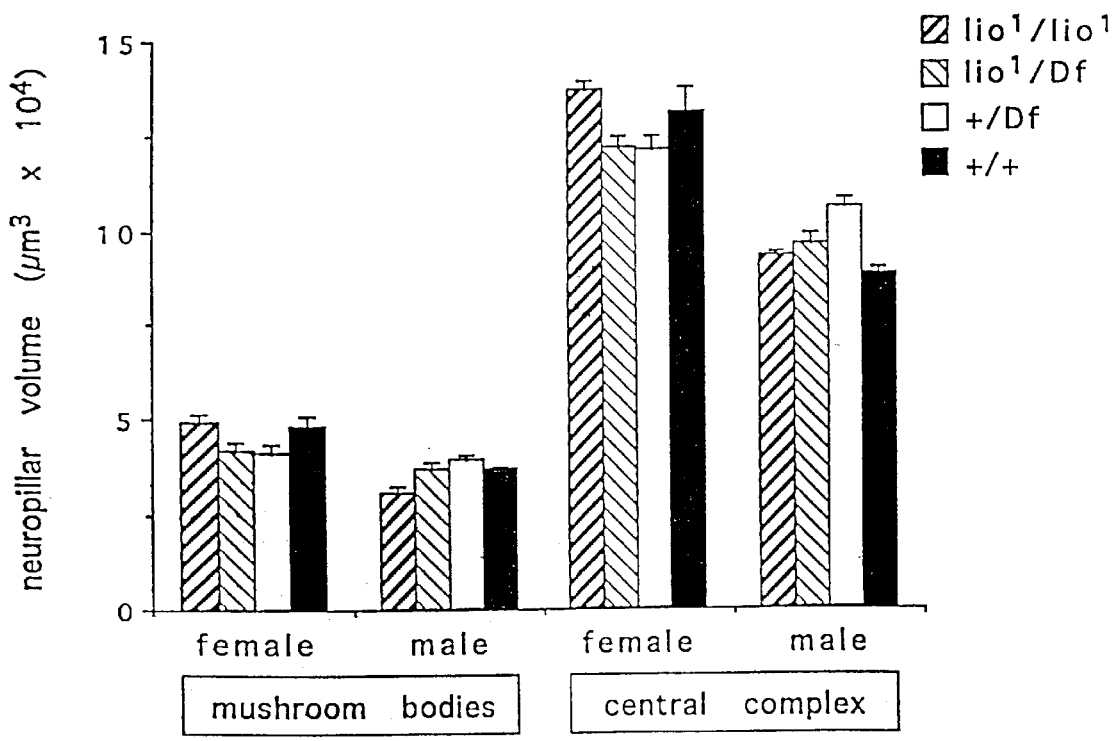
FIG. 6 shows a graphic summary of planimetric determinations of mean (±SEM) neuropilar volumes of the mushroom body calyces and central complexes of wild-type (+/+), +/Df, lio$^1$/Df and lio$^1$/lio$^1$ males and females.

Planimetric estimates of neuropilar volume of mushroom bodies (sum of both hemispheres) and central complex were distributed normally, so raw data were analyzed parametrically with the Macintosh software package JMP 3.1 (SAS Institute, Inc.). Data from each anatomical region were subjected separately to a two-way ANOVA with geno [($F_{(3, 64)}$=1.49, P=0.23) for central complex; ($F_{(3, 64)}$=0.77, P=0.52) for mushroom bodies] and sex [($F_{(1, 64)}$=172.13, P<0.001) for central complex; ($F_{(1, 64)}$=38.68, P<0.001) for mushroom bodies] as main effects and geno x sex [($F_{(3, 64)}$=8.47, P<0.001) for complex; ($F_{(3, 64)}$=6.21, P<0.001) for mushroom bodies] as an interaction term. To maintain an experiment wise error rate of $\alpha$=0.05, critical P values for the four planned comparisons (FIG. 6) were adjusted to P$\leq$0.01. Experimenters were blind to genotype during histological preparations of tissue sections and during planimetric analyses. No significant differences between ++ versus lio$^1$/lio$^1$ or +/Df versus +/lio$^1$ flies were detected in males or females for either anatomical region N=9 flies per genotype for males and 6, 12, 12 and, N=6 files for +/+, +/Df,lio$^1$/Df and lio$^1$/lio$^1$ females, respectively.

Characterization of the Genomic Region Surrounding the linotte P Element Insertion Tagging the linotte gene with a PlacW transposon allowed its immediate localization in situ to cytological region 37 D on the left arm of the second chromosome using P element DNA as a probe (Dura et al. *J. Neurogenet.* 9:1–14 (1993)). The PlacW transposon also contains an origin of DNA replication and ampicillin resistance gene, which allowed the direct cloning of a 900 bp fragment of genomic DNA flanking the linotte$^1$ (lio$^1$) P-element insertion as a bacterial plasmid (see FIG. 1).

This 900 bp genomic DNA fragment was used to probe a Southern blot of wild-type (Canton-S) genomic DNA. The 900 bp probe appeared to be non-repetitive and subsequently was used to screen a Drosophila genomic DNA bacteriophage $\lambda$ library (kindly provided by R. L. Davis). A total of eight genomic clones were recovered; restriction mapping indicated that these covered a 24 kb genomic region (FIG. 1). Cross-hybridization of the 900 bp "rescue fragment" with restriction fragments of the $\lambda$ clones indicated that the linotte P element was inserted in a 1 kb EcoRI-HindIII fragment (FIG. 1). The 900 bp genomic fragment also hybridized in situ to chromosomal region 37 D (data not shown), thereby verifying that the appropriate flanking DNA was cloned.

Cytological localization of the lio$^1$ P element insertion placed it just proximal to the Dopa decarboxylase (Ddc) gene (37 C; Hirsh and Davidson, *Mol. Cell. Biol.* 1:475–485 (1981)). Approximately 180 kb of the genomic region surrounding Ddc had already been cloned by Stathakis et al., *Genetics* (submitted) (1995), so the lio$^1$ and Ddc genomic regions were compared. The most proximal Ddc genomic clone ($\lambda$CS2.27) cross-hybridized with all our $\lambda$ clones on a Southern blot and contained overlapping restriction maps (FIG. 1). This placed the lio$^1$ P element insertion approximately 65 kb proximal to the Ddc locus.

Identification of RNA Transcripts in the linotte Genomic Region

To identify RNA transcripts near the lio$^1$ P element insertion, subcloned restriction fragments from the genomic $\lambda$ clones were used initially to probe Northern blots or wild-type (Canton-S) adult whole-fly polyA+ RNA. A 5.7 kb Hind III fragment distal to the P element insertion (see FIG. 1) hybridized to a 3.5 kb and a 1.9 kb RNA species (data not shown). This 5.7 kb genomic fragment then was used to screen a Canton-S adult head cDNA library (kindly provided by R. L. Davis). Five cDNA clones were identified; cDNA restriction mapping and Southern and Northern blot analyses revealed that these clones fell into two non-crosshybridizing classes. One cDNA class hybridized only to the 1.9 kb RNA transcript and to the 1.2 kb HindIII-SacII genomic fragment (FIG. 1). By these criteria and via direct sequencing of one of the cDNA clones (data not shown), this cDNA class was determined to correspond to the female sterility gene, fs (2)TW1 (see Stathakis et al., *Genetics* submitted (1995). Female fertility appeared normal in the original lio$^1$ mutants and in over 100 lines homozygous for independent excisions of the lio$^1$ P element insertion. Thus, fs(2)TW1 is not likely to correspond to the linotte gene.

The second cDNA class hybridized only to the 3.5 kb RNA transcript and to the 0.9 kb SacII-HindIII genomic fragment situated just 800 bp distal to the lio$^1$ P element insertion (FIG. 1). A 3.1 kb cDNA clone of this class was used as a probe on Northern blots front two independent extractions of polyA+ RNA from wild-type and lio$^1$ P element insertion (FIG. 1). A 3.1 kb cDNA clone of this class was used as a probe on Northern blots from two independent extractions of polyA+ RNA from wild-type and lio$^1$ adult heads, revealing in lio$^1$ mutants 54$\pm$2% of normal levels of the 3.5 kb transcript (see Examples below). The 3.5 kb transcript was detected with only one strand-specific probe from the 3.1 kb cDNA (data not shown), thereby indicating the direction of transcription. Such a Northern blot was also probed with a 6 kb EcoRI genomic restriction fragment (FIG. 1) just proximal to the lio$^1$ P element insertion. No transcripts were detected (data not shown).

Taken together, these data suggested that the linotte gene encodes the 3.5 kb transcript. The linotte P element insertion is approximately 300 bp proximal to chic transcript and the fs(2)TW1 transcript lies immediately distal to this putative linotte transcript (Stathakis et al. *Genetics* (submitted) (1995). The lio$^1$ P element does not appear to be inserted in the transcription unit itself but nevertheless reduces it level of expression, thereby suggesting the lio$^1$ mutation to be hypomorphic. Previously published genetic data (Dura et al., *J. Neurogenet.* 9:1–4 (1993)), in contrast, have suggested that the lio$^1$ mutation is amorphic. Resolution to this apparent discrepancy must await further investigations of the effect of various levels of Lio activity on learning and of the spatial distribution of Lio in adult heads.

Induced Expression of a hslio$^+$ Transgene Rescues the linotte Mutant learning and Memory Deficits Since the linotte mutant strain originally was isolated from a transposon-mediated mutagenesis, this foreign piece of DNA might influence the expression of more than one gene in the region. Thus, no molecular or histological data were sufficient to identify the transcript associated with the linotte learning defect. Correct identification of the lio transcript was obtained, however via transgenic rescue of the linotte learning deficit. The 3.1 kb cDNA clone was fused to the heat shock-70 (hs-70) promoter sequence to construct an inducible hslio⁺ minigene. Several transgenic lines carrying independent genomic insertions of this hslio⁺ construct were generated first on a lio⁺ (wild-type) background. Then the hslio⁺ insertions were crossed into lio¹ mutants.

Mutant linotte flies originally were isolated because of a 3-hour memory retention deficit but subsequently were shown to have impaired learning as well (Dura et al., *J. Neurogenet.* 9:1–14 (1993)). Thus, both learning and 3-hour retention were assayed in hslio⁺ transgenic flies. Our previous experiments have shown robust heat-shock induction of hs-70 promoter-driven transgenes with minimal non-specific effects on learning and memory formation by exposing adults flies to one, 30-minute heat shock (37° C.) three hours before training (Yin et al., *Cell* 79:49–58 (1994); Yin et al., *Cell* 81:107–115 (1995a)). This heat shock regimen was used here.

Figure 3A:
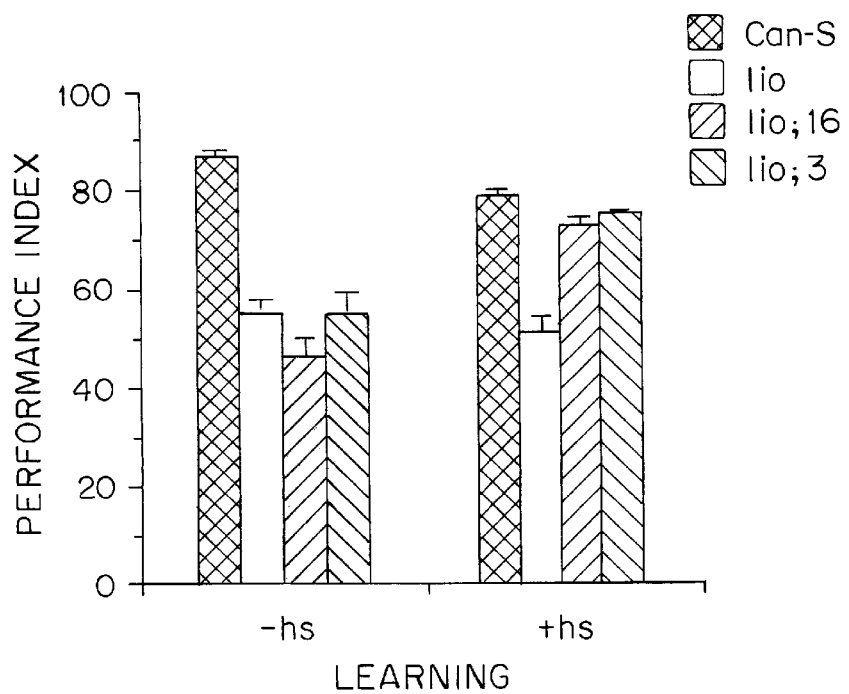
FIGS. 3A and 3B are graphic representations of the rescue of learning and memory deficits of linotte$^1$ (lio$^1$) mutants by heat shock-induced expression of the hslio$^+$ transgene.
Figure 3B:
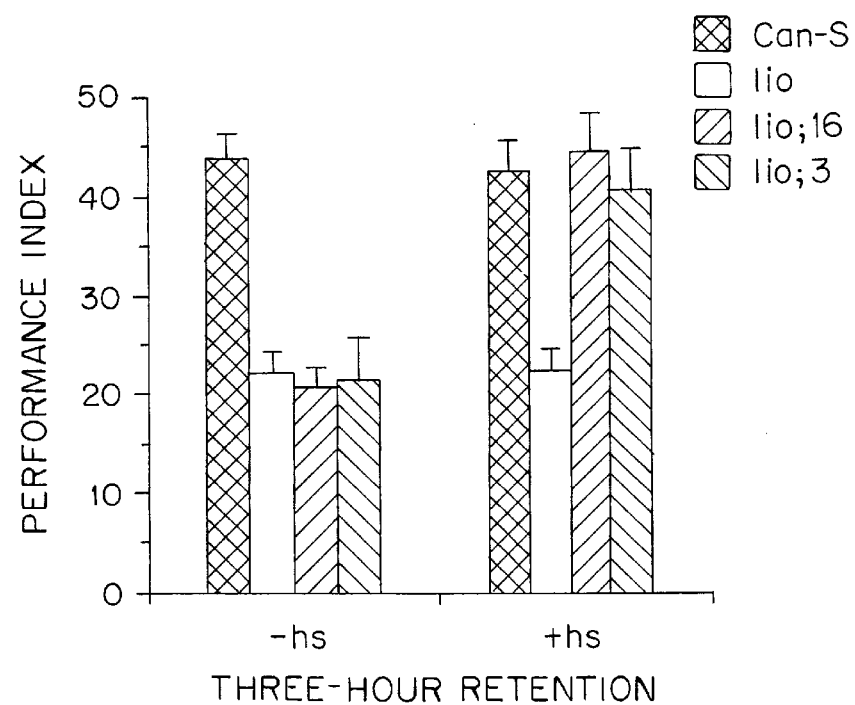

In the absence of heat shock, two hslio⁺ transgenic lines (lio¹; hslio⁺⁻³ and lio¹; hslio⁺-16) displayed learning and 3-hour retention scores similar to those of the lio¹ mutant (FIGS. 3A and 3B). After heat shock-induction of the hslio⁺ transgenes, however, learning and 3-hour retention scores were similar to those of wild-type flies. In contrast, this heat shock regimen had no effect on the learning or 3-hour retention scores of wild-type flies or lio¹ mutants lacking a transgene. Learning also was assayed in two other transgenic lines (lio¹; hslio⁺-1 or lio¹; hslio⁺-21). Mean (PI±SEM) scores for lio¹; hslio⁺-21 transgenic flies were 63±3 (N=6) in the absence of heat shock and 80±2 (N=6) three hours after heat shock, while those for lio¹; hslio⁺-1 were 50±6 (N=2) in the absence of heat shock and 61±2 (N=2) three hours after heat shock. Thus, while results from lio¹; hslio⁺-21 transgenic flies were similar to those of lio¹; $_{hslio}$+-3 and lio¹; hslio⁺-16 transgenic flies, induced expression of the transgene in lio¹; hslio⁺-1 flies appeared to yield intermediate results.

Consistent with the apparent behavioral rescue of the linotte mutation by induced expression of the hslio⁺ transgene, a Northern blot analysis on polyA+ RNA from adult lio¹; hslio⁺-16 heads showed an increased level of expression of the hslio⁺ transcript three hours after heat shock induction, while levels of expression of the endogenous lio⁺ transcript in wild-type, lio¹, or lio¹; hslio⁺-16 flies remained unchanged. The transgenic transcript was undetectable in the absence of heat shock, indicating little leaky expression of the transgene and was again undetectable six hours after heat shock. This same heat shock regimen induces high levels of expression of the hsdCREB2-b or hs-dCREB2-a transgenic transcripts, and they, in contrast, then remain detectable for more than nine hours (Yin et al., *Cell* 79:49–58 (1994); Yin et al., *Cell* 81:107–115 (1995 a)). Thus, turnover of the hslio⁺ transcript appears to be relatively rapid.

Induced Expression of the hslio⁺ Transgene Does Not Affect Olfactory Acuity or Shock Reactivity To understand the effects of single-gene mutations on learning/memory, it has been argued that poor performance in learning/memory assays cannot be interpreted properly without also assessing the task-relevant sensory/motor responses evoked in untrained animals by the stimuli used in the learning/memory procedures (Gailey et al., *J. Comp. Physiol. A*. 169:685–697 (1991); Boynton and Fully, *Genetics* 131:655–672 (1992); Luo et al., *Neuron*. 9:595–605 (1992); Dura et al., *J. Neurogenet*. 9:1–14 (1993); Tully et al., *Cell* 79:35–47 (1994); Yin et al., *Cell* 79:49–58 (1994); Mihalek et al., (submitted 1995); Yin et al., *Cell* 81:107–115 (1995)). As described herein, assays of olfactory acuity and shock reactivity have been developed, which quantify the abilities of the flies to sense the same odors and electroshock in the same T-maze apparatus used for assays of Pavlovian learning/memory. For this study, olfactory acuity and shock reactivity were assayed in untrained flies in the absence of, and three hours after, the usual heat shock regimen. This post-heat shock time point was chosen to correspond to the time when flies were trained in the Pavlovian learning experiments.

Table 1 lists the olfactory acuity and shock reactivity scores from wild-type and transgenic (lio¹; hslio⁺-16) flies with or without the heat shock treatment (±hours) and from mutant lio¹ flies without heat shock. In the absence of heat shock, olfactory acuity and shock reactivity mean scores (PI±SEM) were similar among wild-type, lio¹; hslio⁺-16 and lio¹ flies (cf. Dora et al., *J. Neurogenet*. 9:1–14 (1993)). This observation indicates that the genetic backgrounds of the three strains were similar. Three hours after heat shock, olfactory acuity and shock reactivity mean scores still did not differ between wild-type and lio¹; hslio⁺-16 flies. In light of these data, the behavioral rescue of mutant lio¹ flies by induced expression of tho hslio⁺ transgene observed in Pavlovian learning/memory experiments (see above) now can be interpreted as a specific rescue of learning/memory per se.

TABLE 1

Olfactory acuity and shock reactivity in wild-type (Canton-S), mutant lio¹ and transgenic lio1; hslio⁺-16 flies.

| Heat Shock | Group | Olfactory Acuity[1] | | | | Shock Reactivity | |
| --- | --- | --- | --- | --- | --- | --- | --- |
| | | OCT | | MCH | | | |
| | | $10^0$ | $10^{-2}$ | $10^0$ | $10^{-2}$ | 60 V | 20 V |
| -hs | wild-type lio¹ | 74 ± 3 | 35 ± 7 | 85 ± 3 | 42 ± 7 | 81 ± 5 | 42 ± 10 |
| | | 82 ± 3 | 42 ± 5 | 81 ± 2 | 35 ± 7 | 74 ± 4 | 54 ± 4 |
| -hs | wild-type lio¹; hslio⁺-16 | 69 ± 5 | 44 ± 6 | 72 ± 3 | 33 ± 4 | 87 ± 2 | 62 ± 4 |
| | | 75 ± 4 | 43 ± 6 | 68 ± 4 | 38 ± 5 | 84 ± 3 | 59 ± 6 |

TABLE 1-continued

Olfactory acuity and shock reactivity in wild-type
(Canton-S), mutant lio[1] and transgenic lio1;
hslio[+]-16 flies.

| Heat Shock | Group | Olfactory Acuity[1] | | | | Shock Reactivity | |
|---|---|---|---|---|---|---|---|
| | | OCT | | MCH | | | |
| | | $10^0$ | $10^{-2}$ | $10^0$ | $10^{-2}$ | 60 V | 20 V |
| -hs[2] | wild-type lio[1]; | 52 ± 6 | 31 ± 3 | 62 ± 4 | 21 ± 3 | 87 ± 3 | 57 ± 7 |
| | hslio[+]-16 | 60 ± 6 | 32 ± 5 | 52 ± 3 | 25 ± 5 | 92 ± 1 | 51 ± 6 |

[1]Olfactory acuity and shock reactivity were assayed in untrained flies with the methods of Boynton and Tully Genetics 131:655–672 (1992) and Luo et al. Neuron 9:595–605 (1992), respectively (see Experimental Procedures). N = 8 PIs per group. Planned comparisons between wild-type vs. mutant flies failed to detect any significant differences. $10^0$ corresponds to undiluted odorants, $10^{-2}$ is a 100-fold dilution in mineral oil.
[2]The heat shock regiment was identical to that used for Pavlovian learning/memory assays; flies were assayed 3 hours post heat shock.

Induced Expression of the hslio[+] Transgene Does Not Affect Learning or Memory of Wild-type Flies The issue of whether the improved performance of induced lio[1]; hslio[+]-16 transgenic flies reflects a general enhancement of learning/memory or rather a specific rescue of the linotte mutation was addressed by studying the hslio[+]-16 transgenic insertion in a lio[+] (wild-type) background rather than the lio[1] mutant background. In this manner, the effects on learning and memory of induced (and ectopic) overexpression of the lio[+] transgene were quantified (FIGS. 4A and 4B).

In the absence of heat shock, mean learning or 3-hour retention scores (PI±SEM) did not differ between wild-type and transgenic lio[+]; hslio[+]-16 flies, again indicating that genetic backgrounds of the two strains were similar. When trained three hours after heat shock, mean learning and 3-hour retention scores between these two strains still did not differ. These data demonstrate that induced overexpression of the lio[+] product does not enhance learning or memory generally. Thus, it can be concluded that induced rescue of the learning/memory deficit in lio[1]; hslio[+] transgenic flies (see above) represents a specific rescue of the lio[1] mutation.

The linotte Transcript Encodes a Novel Protein

Full rescue of the lio[1] learning/memory deficits by induced expression of a hslio[+] transgene constitutes definitive proof that the correct RNA transcript had been identified. Thus, a closer (molecular) look at the corresponding 3.1 kb cDNA clone was warranted. Sequence analysis of the 3.1 kb cDNA revealed one prominent 2.7 kb translational open reading frame (ORF) in the transcribed orientation (FIG. 5A). The transcribed orientation of the lio[+] cDNA (SEQ ID NO: 1) was determined by strand-specific probing of a Northern blot of whole-fly Can-S polyA+ RNA. Several stop codons occurred 5' of this putative ORF, and the nucleotides immediately preceding the translational start site conformed with the Drosophila (and general) conservation rules far active translational start sites (Cavener, Nucleic Acids Res. 15:1353–1361 (1987); Kozak, Nucl. Acids. Res. 15:8125–8148 (1987)). Only one reading frame yields a deduced amino acid sequence of appreciable length. This ORF initiates 89 nt from the 5' end of the 3.1 kb cDNA, extends 2748 nt and terminates 262 nt from the 3' end.

This ORF dencodes a 916 amino acid, 103 kD deduced polypeptide (SEQ ID NO: 2) and terminates 800 nt upstream of the 3' end of the cDNA sequence. The deduced amino acid sequence (FIG. 5B, SEQ ID NO: 2) bears no significant homology to any previously characterized protein in the BLAST, Swiss-Protein or Pro-Site databases. The linotte gene, therefore, appears to encode a novel protein involved in associative learning.

The lio[+] Transcript is Detected in Embryos, Pupae and Adults But Not Larvae

To investigate the developmental expression of the linotte transcript, the 3.1 kb cDNA was used in Northern blot analyses to probe polyA+ RNA from various developmental stages. At all stages, only one 3.5 kb transcript was detected. Levels of expression of this message differed significantly during development. The lio[+] mRNA was expressed at a high level in early embryos (0–4 hours) but is not in late embryos (>16 hours), suggesting a maternal origin for the early signal. The lio[+] message was not detected during the larval stages but then reappeared during pupal development and was expressed at high levels in adult head and body.

The Developmental Pattern of Expression of the Enhancer-trap Reporter Gene in lio[1] Mutants Does Not Correspond to that of the lio[+] Transcript The lio[1] mutation resulted from the insertion of a transposable enhancer-trap P element (PlacW) containing a lacZ reporter gene, which could be activated transcriptionally by regional enhancer elements (Bier et al., Genes Dev. 3:1273–1287 (1989)). New mutant alleles of rutabaga, for instance, were recovered with PlacW insertions in the 5' untranslated region of the gene (Levin et al., Cell 68:479–489 (1992)). The pattern of lacZ reporter gene expression in these mutants overlapped extensively with rut protein expression (Han et al., Neuron 9:619–627 (1992)).

To observe lacZ reporter gene activity in the CNS of linotte mutants, embryos, third-instar larvae and adults were stained with the chromogenic lacZ substrate, X-gal. lacZ activity in a whole-mount stage 14 embryo (100×) was detected in the brain and in the ventral nerve cord. lacZ activity also was detected in the peripheral nervous system and in the posterior midgut. In whole-mount, dissected third-instar larval CNSs (200×), enhancer trap-driven expression of the lacZ reporter gene was appreciable in the dorsal-medial region of the brain, in the lateral brain hemispheres, the developing adult visual system and in the ventral ganglia. In 10 μm frontal sections of adult heads (200×), enhancer trap-driven expression of the lacZ reporter gene was observed in the dorsal-medial region, in the optic lobes and in the subesophogeal ganglion. No staining was apparent in cells surrounding the mushroom body calyces (data not shown).

In stage 12 embryos lacZ reporter gene activity was detected in the central and peripheral nervous systems and in several other locations. In third-instar larvae, a high level of lacZ reporter gene activity was observed in the lateral hemispheres of the brain lobes, where the adult visual system develops, and to a lesser degree in the dorsal medial region of the brain and in the ventral ganglia. In frontal sections of adult heads, lacZ reporter gene activity also was observed in a few neurons in the dorsal medial region of the protocerebrum and in the optic lobes and subesophogeal ganglion. No prominent lacZ activity was detected in the calyces of the mushroom bodies, where the dunce and rutabaga genes are preferentially expressed (Nighorn et al., *Neuron* 6:455–467 (1991); Han et al., *Neuron* 9:619–627 (1992)). Notably, this developmental pattern of lacZ expression does not coincide with the temporal pattern of lio$^+$ expression (data not shown).

Gross Anatomy of Mushroom Bodies and Central Complex is Normal in linotte Mutants Genetic or chemical lesions of two anatomical regions of the adult brain, the mushroom bodies and the central complex, disrupt olfactory learning (Heisenberg et al., *J. Neurogenet* 2:1–30 (1985); de Belle and Heisenberg, *Science* 263:692–695 (1994)). Subtler aspects of mushroom body development also are defective in dunce and rutabaga mutants (Balling, *J. Neurogenetics* 4:65–73 (1987)), and defects in the central complex, in fact, have been reported for linotte mutants (Dura et al.,*J. Neurogenet* 10:25 (1995)).

Full rescue of the lio$^1$ learning/memory deficit by induced expression of the hs-lio$^+$ transgenc in adults (see above) brought into question the latter claim, however. Thus, adult brain structure in lio$^1$ mutants were reassessed. Mushroom bodies and central complex were visually inspected, and their neuropilar volumes were quantified via planimetric analysis in wild-type (lio$^+$) flies, lio$^1$ homozygous mutants and hemizygous flies carrying either the wild-type (lio$^+$) or lio$^1$ chromosome and a second chromosome deletion (Df, see Experimental Procedures) of the linotte region. (The dosages of lio$^+$ or lio$^1$ in these hemizygous flies were only 50% of those in corresponding homozygous flies, thereby potentially yielding more severe phenotypic defects). In a double-blind experiment, frontal sections of lio$^1$/lio$^1$,lio$^1$/Df,lio$^+$/Df and lio$^+$/lio$^+$ heads were serially sectioned in the laboratory of Dr. M. Heisenberg, and then planimetric analyses of mushroom bodies and central complex were carried out in our laboratory. The different preparations were fixed, embedded in paraffin, cut into 7 $\mu$m sections and inspected by fluorescence microscopy (400×). These analyses failed to detect any (qualitative or quantitative differences among the four genotypes in these two brain structures (data not shown).

Equivalents

Those skilled in the art will recognize or be able to ascertain, using no more than routine experimentation, many equivalents to the specific embodiments of the invention described herein. Such equivalents are intended to be encompassed in the scope of the following claims.

We claim:

1. Isolated DNA which functions in associative learning, said DNA consisting of the DNA sequence of SEQ ID NO: 1.

2. Isolated DNA according to claim 1, wherein disruption of said gene results in decreased associative learning and/or memory.

3. An isolated nucleic acid sequence consisting of the nucleic acid sequence of SEQ ID NO: 1 or the complement of said nucleic acid sequence.

4. An isolated DNA encoding the amino acid sequence of SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3098 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 89..2833

( x i ) SEQUENCE DESCRIPTION: SEQ ID NO:1:

```
CTGAGAAGCG  CGCAACGTGC  ACACTGGCAG  GCTGATTGAA  AAAATTCGTT  GCAAATGTTT              60

ATGTACAAAT  ATTGAATAAA  AAATAAAA ATG CTG CGG CAG GAG AAC TTG GCA                   112
                                 Met Leu Arg Gln Glu Asn Leu Ala
                                  1               5

GCC AAC TTC TGC GGT CTC CTG GCC AGC CAG GGC TAT AAA GAG AAG GCA                   160
Ala Asn Phe Cys Gly Leu Leu Ala Ser Gln Gly Tyr Lys Glu Lys Ala
     10              15                  20

AAC GAG TGG CGC ATT TTG GGC CAG GAA CAG GAT GGA TCT CTG CTC ACG                   208
Asn Glu Trp Arg Ile Leu Gly Gln Glu Gln Asp Gly Ser Leu Leu Thr
 25              30                  35                      40

TCC TGG ATA TTC GAG TAC GCG GAC GAG GAT CAG CGC AAG GAG ACG TGC                   256
Ser Trp Ile Phe Glu Tyr Ala Asp Glu Asp Gln Arg Lys Glu Thr Cys
                 45                  50                  55

ATT GGC CAC TTT CAC GCC ACC AAG AAG CAG CTG CGA CTC CTT TGG ACC                   304
Ile Gly His Phe His Ala Thr Lys Lys Gln Leu Arg Leu Leu Trp Thr
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 60  |     |     |     |     | 65  |     |     |     |     | 70  |     |      |
| CTC | GAC | AAT | TGC | CGT | GAG | ATC | GTC | CAG | GCA | ACG | ATT | AAC | AGC | AGT | GTC | 352  |
| Leu | Asp | Asn | Cys | Arg | Glu | Ile | Val | Gln | Ala | Thr | Ile | Asn | Ser | Ser | Val |      |
|     |     | 75  |     |     |     |     | 80  |     |     |     |     | 85  |     |     |     |      |
| ACA | TTG | CTG | TCC | TTC | GTG | GAG | AAA | ACT | GAG | GGC | AAG | CTC | TAT | CAG | GCC | 400  |
| Thr | Leu | Leu | Ser | Phe | Val | Glu | Lys | Thr | Glu | Gly | Lys | Leu | Tyr | Gln | Ala |      |
|     |     | 90  |     |     |     |     | 95  |     |     |     |     | 100 |     |     |     |      |
| TTT | GTC | GTG | GAG | GTA | AGG | AGC | TCC | GAA | GGT | GGC | ACG | GCC | ACG | CCC | CTC | 448  |
| Phe | Val | Val | Glu | Val | Arg | Ser | Ser | Glu | Gly | Gly | Thr | Ala | Thr | Pro | Leu |      |
| 105 |     |     |     |     | 110 |     |     |     |     | 115 |     |     |     |     | 120 |      |
| AAC | TCG | GAG | CCC | TCC | AAC | CGC | CAG | ATG | ATG | ACG | CAG | TTC | CTG | TGG | CGC | 496  |
| Asn | Ser | Glu | Pro | Ser | Asn | Arg | Gln | Met | Met | Thr | Gln | Phe | Leu | Trp | Arg |      |
|     |     |     |     | 125 |     |     |     |     | 130 |     |     |     |     | 135 |     |      |
| GTC | GAG | AGT | GCC | ACG | CGC | ACC | TGC | TGG | CAG | GAC | AAG | CTA | CTG | GTG | CTC | 544  |
| Val | Glu | Ser | Ala | Thr | Arg | Thr | Cys | Trp | Gln | Asp | Lys | Leu | Leu | Val | Leu |      |
|     |     |     | 140 |     |     |     |     | 145 |     |     |     |     | 150 |     |     |      |
| ACC | CAC | GAG | GAA | TCC | ATC | AAG | CAG | TAC | AGC | TGC | GTG | GTC | AAG | CAG | AGC | 592  |
| Thr | His | Glu | Glu | Ser | Ile | Lys | Gln | Tyr | Ser | Cys | Val | Val | Lys | Gln | Ser |      |
|     |     | 155 |     |     |     |     | 160 |     |     |     |     | 165 |     |     |     |      |
| TCC | ACC | ACA | TGC | TCG | ACT | GGC | GGA | GGC | GAG | GGC | AGC | GCC | TGG | AGG | CTA | 640  |
| Ser | Thr | Thr | Cys | Ser | Thr | Gly | Gly | Gly | Glu | Gly | Ser | Ala | Trp | Arg | Leu |      |
|     | 170 |     |     |     |     | 175 |     |     |     |     | 180 |     |     |     |     |      |
| GAC | ACC | AGC | ATA | CTG | ACC | TAC | GAA | ACG | CTG | GCC | AGG | AAC | TTT | AGC | TGG | 688  |
| Asp | Thr | Ser | Ile | Leu | Thr | Tyr | Glu | Thr | Leu | Ala | Arg | Asn | Phe | Ser | Trp |      |
| 185 |     |     |     |     | 190 |     |     |     |     | 195 |     |     |     |     | 200 |      |
| GCC | CAG | TGG | GAT | CCC | GAG | TGC | CAG | GCT | CTT | TAT | TAC | ATT | CAC | TTG | AAG | 736  |
| Ala | Gln | Trp | Asp | Pro | Glu | Cys | Gln | Ala | Leu | Tyr | Tyr | Ile | His | Leu | Lys |      |
|     |     |     |     | 205 |     |     |     |     | 210 |     |     |     |     | 215 |     |      |
| CCG | AAG | GCC | AAG | AGC | CTC | AGT | CTG | CTG | GAC | GAG | AGG | GAG | GAG | GCT | GGC | 784  |
| Pro | Lys | Ala | Lys | Ser | Leu | Ser | Leu | Leu | Asp | Glu | Arg | Glu | Glu | Ala | Gly |      |
|     |     |     | 220 |     |     |     |     | 225 |     |     |     |     | 230 |     |     |      |
| GAG | CAG | ACA | ACT | CCT | ACT | TTA | AGC | CCC | ACG | CTC | TCC | GCC | TTT | CAG | TTT | 832  |
| Glu | Gln | Thr | Thr | Pro | Thr | Leu | Ser | Pro | Thr | Leu | Ser | Ala | Phe | Gln | Phe |      |
|     |     | 235 |     |     |     |     | 240 |     |     |     |     | 245 |     |     |     |      |
| AAC | GAA | AAA | CAG | CCA | ACG | GAA | ACA | GTG | CTT | AAT | ATA | CCC | CTC | AAT | TTG | 880  |
| Asn | Glu | Lys | Gln | Pro | Thr | Glu | Thr | Val | Leu | Asn | Ile | Pro | Leu | Asn | Leu |      |
| 250 |     |     |     |     | 255 |     |     |     |     | 260 |     |     |     |     |     |      |
| CCA | AAG | CTG | CCC | AAT | GGC | TCC | AAA | GAG | GAA | TCG | CCA | AGC | TAC | GAT | GAC | 928  |
| Pro | Lys | Leu | Pro | Asn | Gly | Ser | Lys | Glu | Glu | Ser | Pro | Ser | Tyr | Asp | Asp |      |
| 265 |     |     |     | 270 |     |     |     |     | 275 |     |     |     |     | 280 |     |      |
| GAT | GCG | GTT | CCC | TTG | CGC | GTG | CAC | GAT | AGT | TCG | CTA | AAT | CTC | ATC | ATA | 976  |
| Asp | Ala | Val | Pro | Leu | Arg | Val | His | Asp | Ser | Ser | Leu | Asn | Leu | Ile | Ile |      |
|     |     |     |     | 285 |     |     |     |     | 290 |     |     |     |     | 295 |     |      |
| CTG | GCG | GAC | ACC | TCG | GGC | ATG | TTT | TTC | GTC | TGT | CAC | TAC | TAC | CTG | TAC | 1024 |
| Leu | Ala | Asp | Thr | Ser | Gly | Met | Phe | Phe | Val | Cys | His | Tyr | Tyr | Leu | Tyr |      |
|     |     |     | 300 |     |     |     |     | 305 |     |     |     |     | 310 |     |     |      |
| CAG | CCG | ATG | CAG | TCG | GAG | CAA | AGG | GAT | GTG | CAC | TTT | GCC | TAC | TCG | GTG | 1072 |
| Gln | Pro | Met | Gln | Ser | Glu | Gln | Arg | Asp | Val | His | Phe | Ala | Tyr | Ser | Val |      |
|     |     | 315 |     |     |     |     | 320 |     |     |     |     | 325 |     |     |     |      |
| ACT | TTG | CTT | CAC | CAC | GGC | TGT | GTG | GTG | CAC | TGC | GTC | ATG | CCC | GGT | GTG | 1120 |
| Thr | Leu | Leu | His | His | Gly | Cys | Val | Val | His | Cys | Val | Met | Pro | Gly | Val |      |
|     | 330 |     |     |     |     | 335 |     |     |     |     | 340 |     |     |     |     |      |
| CCG | TGG | CAA | AAG | GCC | CGT | CTG | CTG | AGG | CCA | ACA | TTT | GCG | CTA | CAC | GGC | 1168 |
| Pro | Trp | Gln | Lys | Ala | Arg | Leu | Leu | Arg | Pro | Thr | Phe | Ala | Leu | His | Gly |      |
| 345 |     |     |     |     | 350 |     |     |     |     | 355 |     |     |     |     | 360 |      |
| CAG | CAT | CAC | TTG | CTG | GTG | TCG | TCC | GCC | TTT | TTT | GTC | CAC | CTC | TTG | GAC | 1216 |
| Gln | His | His | Leu | Leu | Val | Ser | Ser | Ala | Phe | Phe | Val | His | Leu | Leu | Asp |      |
|     |     |     |     | 365 |     |     |     |     | 370 |     |     |     |     | 375 |     |      |
| GTG | GGA | CTG | CAG | CAC | GAA | CCG | AAC | TGC | CAT | ATC | GTG | TGT | GCA | GCC | CAC | 1264 |
| Val | Gly | Leu | Gln | His | Glu | Pro | Asn | Cys | His | Ile | Val | Cys | Ala | Ala | His |      |

|     |     |     |     |     | 380 |     |     |     |     | 385 |     |     |     |     | 390 |      |
| --- | --- | --- | --- | --- | --- | --- | --- | --- | --- | --- | --- | --- | --- | --- | --- | ---- |
| AAT | CGA | AGT | CCC | GAT | ATC | ACA | CAG | CTG | GTG | CCT | TTG | CGA | AAG | TGG | GGA | 1312 |
| Asn | Arg | Ser | Pro | Asp | Ile | Thr | Gln | Leu | Val | Pro | Leu | Arg | Lys | Trp | Gly |      |
|     |     | 395 |     |     |     |     | 400 |     |     |     |     | 405 |     |     |     |      |
| GCT | CTG | GCT | TAT | GAT | GCG | GCT | ACC | TTG | GAT | CTG | GTC | TCG | TTG | TCC | GTG | 1360 |
| Ala | Leu | Ala | Tyr | Asp | Ala | Ala | Thr | Leu | Asp | Leu | Val | Ser | Leu | Ser | Val |      |
|     |     | 410 |     |     |     |     | 415 |     |     |     |     | 420 |     |     |     |      |
| CCC | AAA | TCC | CAT | TTG | ATA | GAG | GCT | TTC | CGC | AAT | GAC | AGT | TCG | CTG | GAC | 1408 |
| Pro | Lys | Ser | His | Leu | Ile | Glu | Ala | Phe | Arg | Asn | Asp | Ser | Ser | Leu | Asp |      |
| 425 |     |     |     |     | 430 |     |     |     |     | 435 |     |     |     |     | 440 |      |
| AAT | AGA | ATC | AGC | ATT | ATC | CAC | TAC | TTC | CTT | TTC | GAC | TCG | AAC | GAT | ATG | 1456 |
| Asn | Arg | Ile | Ser | Ile | Ile | His | Tyr | Phe | Leu | Phe | Asp | Ser | Asn | Asp | Met |      |
|     |     |     |     | 445 |     |     |     |     | 450 |     |     |     |     | 455 |     |      |
| GAT | GTG | TTG | GCC | GAG | CTG | CTG | AAC | AAT | ATC | TTG | GAG | CGA | CCA | CTC | TCC | 1504 |
| Asp | Val | Leu | Ala | Glu | Leu | Leu | Asn | Asn | Ile | Leu | Glu | Arg | Pro | Leu | Ser |      |
|     |     |     | 460 |     |     |     |     | 465 |     |     |     |     | 470 |     |     |      |
| CTG | GAT | ACG | GTG | GCT | TTG | CTG | AAG | GAG | GCT | CTT | GTG | GCT | GGC | AGC | TAT | 1552 |
| Leu | Asp | Thr | Val | Ala | Leu | Leu | Lys | Glu | Ala | Leu | Val | Ala | Gly | Ser | Tyr |      |
|     |     | 475 |     |     |     |     | 480 |     |     |     |     | 485 |     |     |     |      |
| GCG | GCT | GCT | GTT | CGC | GGA | CTA | CCA | GAG | GAT | GCC | AAG | CCA | CTG | ATG | CGA | 1600 |
| Ala | Ala | Ala | Val | Arg | Gly | Leu | Pro | Glu | Asp | Ala | Lys | Pro | Leu | Met | Arg |      |
|     | 490 |     |     |     |     | 495 |     |     |     |     | 500 |     |     |     |     |      |
| CTA | CTG | CCA | TTG | ACT | ACT | GCC | TTA | GCC | TCG | CGA | CCA | ATC | CTC | GCA | AAG | 1648 |
| Leu | Leu | Pro | Leu | Thr | Thr | Ala | Leu | Ala | Ser | Arg | Pro | Ile | Leu | Ala | Lys |      |
| 505 |     |     |     |     | 510 |     |     |     |     | 515 |     |     |     |     | 520 |      |
| GTG | GCC | GAT | ATA | AGC | GTG | GGT | CTC | TCT | CAT | GAA | ACC | CTG | CAC | AAT | ACC | 1696 |
| Val | Ala | Asp | Ile | Ser | Val | Gly | Leu | Ser | His | Glu | Thr | Leu | His | Asn | Thr |      |
|     |     |     |     | 525 |     |     |     |     | 530 |     |     |     |     | 535 |     |      |
| AGC | ATG | ATG | CTG | CTC | TCG | CCA | CAG | CAG | CGC | CTT | TCA | CCT | TAT | CGC | ACG | 1744 |
| Ser | Met | Met | Leu | Leu | Ser | Pro | Gln | Gln | Arg | Leu | Ser | Pro | Tyr | Arg | Thr |      |
|     |     |     | 540 |     |     |     |     | 545 |     |     |     |     | 550 |     |     |      |
| GAC | ATC | TGG | ACT | CGC | TTA | TGG | GAC | CTT | CTC | AAC | GAG | TCA | GCC | AAG | CAG | 1792 |
| Asp | Ile | Trp | Thr | Arg | Leu | Trp | Asp | Leu | Leu | Asn | Glu | Ser | Ala | Lys | Gln |      |
|     |     | 555 |     |     |     |     | 560 |     |     |     |     | 565 |     |     |     |      |
| GAG | CAG | CCT | AGA | TTC | AGT | GCT | GAG | CAG | GTG | ACG | GAG | AAG | TTG | ATC | TTT | 1840 |
| Glu | Gln | Pro | Arg | Phe | Ser | Ala | Glu | Gln | Val | Thr | Glu | Lys | Leu | Ile | Phe |      |
|     | 570 |     |     |     |     | 575 |     |     |     |     | 580 |     |     |     |     |      |
| AGT | TTG | GCC | TGC | TAC | CAG | CCG | GAG | GCT | CTG | TCC | AGA | TGC | ACC | ACG | CCA | 1888 |
| Ser | Leu | Ala | Cys | Tyr | Gln | Pro | Glu | Ala | Leu | Ser | Arg | Cys | Thr | Thr | Pro |      |
| 585 |     |     |     |     | 590 |     |     |     |     | 595 |     |     |     |     | 600 |      |
| CTT | TCG | CCA | GAC | ACG | GGC | ACC | GGT | GGA | TTT | GGT | GAC | TAT | AGT | AGC | GGA | 1936 |
| Leu | Ser | Pro | Asp | Thr | Gly | Thr | Gly | Gly | Phe | Gly | Asp | Tyr | Ser | Ser | Gly |      |
|     |     |     |     | 605 |     |     |     |     | 610 |     |     |     |     | 615 |     |      |
| AGT | GCT | TTT | CCA | TTC | AGC | AAC | GAA | GTG | CTG | CCC | TTT | ATC | GAA | CTG | GAG | 1984 |
| Ser | Ala | Phe | Pro | Phe | Ser | Asn | Glu | Val | Leu | Pro | Phe | Ile | Glu | Leu | Glu |      |
|     |     |     | 620 |     |     |     |     | 625 |     |     |     |     | 630 |     |     |      |
| GGA | TGC | ACA | GCC | AGC | AAG | CAG | GAG | CAC | GTC | ATT | TCT | GTG | TAT | CTG | CGC | 2032 |
| Gly | Cys | Thr | Ala | Ser | Lys | Gln | Glu | His | Val | Ile | Ser | Val | Tyr | Leu | Arg |      |
|     |     | 635 |     |     |     |     | 640 |     |     |     |     | 645 |     |     |     |      |
| GAG | CTG | AGC | GTT | CAC | CTG | GTG | AAG | CAC | ACG | TCA | AAG | CCC | AAC | ACT | GGC | 2080 |
| Glu | Leu | Ser | Val | His | Leu | Val | Lys | His | Thr | Ser | Lys | Pro | Asn | Thr | Gly |      |
|     | 650 |     |     |     |     | 655 |     |     |     |     | 660 |     |     |     |     |      |
| TTC | CGT | TGG | CTG | AAG | GAG | ACC | TTT | TTC | GAG | CGC | TCC | CAG | GCT | CCA | GCT | 2128 |
| Phe | Arg | Trp | Leu | Lys | Glu | Thr | Phe | Phe | Glu | Arg | Ser | Gln | Ala | Pro | Ala |      |
| 665 |     |     |     |     | 670 |     |     |     |     | 675 |     |     |     |     | 680 |      |
| CAT | GTG | CAT | GCG | GTG | GCC | TCG | CAG | TTC | GTT | TCC | GCG | CAG | CTT | GAA | CTC | 2176 |
| His | Val | His | Ala | Val | Ala | Ser | Gln | Phe | Val | Ser | Ala | Gln | Leu | Glu | Leu |      |
|     |     |     |     | 685 |     |     |     |     | 690 |     |     |     |     | 695 |     |      |
| TCG | CGG | GCT | CTT | TGC | TCT | CTG | GTT | TGT | CGT | GCT | GCA | GGC | CTA | GAT | GCG | 2224 |
| Ser | Arg | Ala | Leu | Cys | Ser | Leu | Val | Cys | Arg | Ala | Ala | Gly | Leu | Asp | Ala |      |

| | | | | | | | | | | | | | | | | |
|---|---|---|---|---|---|---|---|---|---|---|---|---|---|---|---|---|
| | | 700 | | | | | 705 | | | | | 710 | | | | |
| CGC | ATG | GAG | ACC | TCG | AGG | GGT | TTT | CAG | TTG | ATT | GAC | CAA | ATG | GCT | GCC | 2272 |
| Arg | Met | Glu | Thr | Ser | Arg | Gly | Phe | Gln | Leu | Ile | Asp | Gln | Met | Ala | Ala | |
| | | 715 | | | | | 720 | | | | | 725 | | | | |
| AAT | CAA | CAG | CAC | TCT | CTG | TTT | CTA | ATC | CTC | GAG | CGC | TAT | TGC | CTG | GCT | 2320 |
| Asn | Gln | Gln | His | Ser | Leu | Phe | Leu | Ile | Leu | Glu | Arg | Tyr | Cys | Leu | Ala | |
| | | 730 | | | | | 735 | | | | | 740 | | | | |
| GTG | GAA | TCA | ATT | GCG | TTT | CCC | CTG | CCC | GAG | GGT | TTC | TCC | TCG | TTC | TTC | 2368 |
| Val | Glu | Ser | Ile | Ala | Phe | Pro | Leu | Pro | Glu | Gly | Phe | Ser | Ser | Phe | Phe | |
| 745 | | | | | 750 | | | | | 755 | | | | | 760 | |
| ACC | TAC | TTG | GGC | TAT | CGT | GCG | CTG | GGC | TAT | GAT | ATG | TTT | CTG | CAG | TAT | 2416 |
| Thr | Tyr | Leu | Gly | Tyr | Arg | Ala | Leu | Gly | Tyr | Asp | Met | Phe | Leu | Gln | Tyr | |
| | | | | 765 | | | | | 770 | | | | | 775 | | |
| GTG | GAA | AAT | CAT | GTG | TTC | GAA | CTG | CAA | GTG | GAT | GTG | ATG | AAG | GCC | ATT | 2464 |
| Val | Glu | Asn | His | Val | Phe | Glu | Leu | Gln | Val | Asp | Val | Met | Lys | Ala | Ile | |
| | | | 780 | | | | | 785 | | | | | 790 | | | |
| GTT | TTC | GAT | ATT | GAA | GAT | TCT | CCA | CTA | GGC | ATT | GAG | CGG | AAG | CTA | TCA | 2512 |
| Val | Phe | Asp | Ile | Glu | Asp | Ser | Pro | Leu | Gly | Ile | Glu | Arg | Lys | Leu | Ser | |
| | | 795 | | | | | 800 | | | | | 805 | | | | |
| CTT | TTG | TCT | GCT | CTG | CCC | AAG | CAG | CGT | GCT | CAA | AGG | TTA | CTC | AAA | TGC | 2560 |
| Leu | Leu | Ser | Ala | Leu | Pro | Lys | Gln | Arg | Ala | Gln | Arg | Leu | Leu | Lys | Cys | |
| | 810 | | | | | 815 | | | | | 820 | | | | | |
| TGG | CAG | CAT | CCG | GAC | AGC | CTT | ATG | ATC | CGC | GGA | CGC | GAG | CAT | GCG | GCC | 2608 |
| Trp | Gln | His | Pro | Asp | Ser | Leu | Met | Ile | Arg | Gly | Arg | Glu | His | Ala | Ala | |
| 825 | | | | | 830 | | | | | 835 | | | | | 840 | |
| AAC | ATT | CTG | TCG | GGT | CAG | CAG | CAG | GAG | GTG | TTG | CAC | CAG | CAG | CGA | CCC | 2656 |
| Asn | Ile | Leu | Ser | Gly | Gln | Gln | Gln | Glu | Val | Leu | His | Gln | Gln | Arg | Pro | |
| | | | | 845 | | | | | 850 | | | | | 855 | | |
| ACG | GCC | TGC | GTG | AAT | CAA | TCG | CGA | AAT | AAT | GGC | CGG | AGC | GAT | CTA | ACT | 2704 |
| Thr | Ala | Cys | Val | Asn | Gln | Ser | Arg | Asn | Asn | Gly | Arg | Ser | Asp | Leu | Thr | |
| | | | 860 | | | | | 865 | | | | | 870 | | | |
| GCC | GAA | GCC | CTT | TCG | CCA | CTG | GAC | TCC | TTT | CTG | GAC | CTG | CTG | ACT | GCG | 2752 |
| Ala | Glu | Ala | Leu | Ser | Pro | Leu | Asp | Ser | Phe | Leu | Asp | Leu | Leu | Thr | Ala | |
| | | 875 | | | | | 880 | | | | | 885 | | | | |
| AAG | GCC | AGT | CTA | AAC | GAA | TTG | GAC | TAC | AAT | CTG | CTT | ATT | GAA | ACT | ACT | 2800 |
| Lys | Ala | Ser | Leu | Asn | Glu | Leu | Asp | Tyr | Asn | Leu | Leu | Ile | Glu | Thr | Thr | |
| | | 890 | | | | | 895 | | | | | 900 | | | | |
| CTA | AGC | TCC | ATC | GAT | CAG | CTG | AAA | CTG | GAG | GCA | TGAATTTAAT | | GTTAAGAGTA | | | 2853 |
| Leu | Ser | Ser | Ile | Asp | Gln | Leu | Lys | Leu | Glu | Ala | | | | | | |
| 905 | | | | | 910 | | | | | 915 | | | | | | |
| ACTAATGAAG | TATTGTGTCA | AATTATCAAG | TACTTAGCCA | AGGCCAGTTT | GCAAATATTC | | | | | | | | | | | 2913 |
| CAAAGATTTG | ATTTGTCAAA | TGTATTAGTT | AAGATTCTTC | TCGTGCAGCT | TTGATTTTTG | | | | | | | | | | | 2973 |
| TTAGGGTTCT | TCTGTGTGCT | TTTAGTATTA | ATTTTCTGTT | CCTATAATTT | GTGTAACGAC | | | | | | | | | | | 3033 |
| TGATACACAT | TCCAAGTCTG | TAATTATAAA | TTATTTATGT | TGTTAATTGA | TGTACCTAAA | | | | | | | | | | | 3093 |
| AAAAA | | | | | | | | | | | | | | | | 3098 |

( 2 ) INFORMATION FOR SEQ ID NO:2:

( i ) SEQUENCE CHARACTERISTICS:
        ( A ) LENGTH: 915 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Leu | Arg | Gln | Glu | Asn | Leu | Ala | Ala | Asn | Phe | Cys | Gly | Leu | Leu | Ala |
|---|---|---|---|---|---|---|---|---|---|---|---|---|---|---|---|
| 1 | | | | 5 | | | | | 10 | | | | | 15 | |
| Ser | Gln | Gly | Tyr | Lys | Glu | Lys | Ala | Asn | Glu | Trp | Arg | Ile | Leu | Gly | Gln |

|         |         |         |         |         |         |         |         |         |         |         |         |         |         |
|---------|---------|---------|---------|---------|---------|---------|---------|---------|---------|---------|---------|---------|---------|
|         |         |         |         | 20      |         |         |         | 25      |         |         |         | 30      |         |
| Glu | Gln | Asp | Gly<br>35 | Ser | Leu | Leu | Thr<br>40 | Ser | Trp | Ile | Phe | Glu<br>45 | Tyr | Ala | Asp |
| Glu | Asp | Gln<br>50 | Arg | Lys | Glu | Thr<br>55 | Cys | Ile | Gly | His | Phe<br>60 | His | Ala | Thr | Lys |
| Lys<br>65 | Gln | Leu | Arg | Leu | Leu<br>70 | Trp | Thr | Leu | Asp | Asn<br>75 | Cys | Arg | Glu | Ile | Val<br>80 |
| Gln | Ala | Thr | Ile | Asn<br>85 | Ser | Ser | Val | Thr | Leu<br>90 | Leu | Ser | Phe | Val | Glu<br>95 | Lys |
| Thr | Glu | Gly | Lys<br>100 | Leu | Tyr | Gln | Ala | Phe<br>105 | Val | Val | Glu | Val | Arg<br>110 | Ser | Ser |
| Glu | Gly | Gly | Thr<br>115 | Ala | Thr | Pro | Leu | Asn<br>120 | Ser | Glu | Pro | Ser<br>125 | Asn | Arg | Gln |
| Met | Met<br>130 | Thr | Gln | Phe | Leu | Trp<br>135 | Arg | Val | Glu | Ser | Ala<br>140 | Thr | Arg | Thr | Cys |
| Trp<br>145 | Gln | Asp | Lys | Leu | Leu<br>150 | Val | Leu | Thr | His | Glu<br>155 | Ser | Ile | Lys | Gln<br>160 |
| Tyr | Ser | Cys | Val | Val<br>165 | Lys | Gln | Ser | Ser | Thr<br>170 | Thr | Cys | Ser | Thr | Gly<br>175 | Gly |
| Gly | Glu | Gly | Ser<br>180 | Ala | Trp | Arg | Leu | Asp<br>185 | Thr | Ser | Ile | Leu | Thr<br>190 | Tyr | Glu |
| Thr | Leu | Ala | Arg<br>195 | Asn | Phe | Ser | Trp | Ala<br>200 | Gln | Trp | Asp | Pro | Glu<br>205 | Cys | Gln |
| Ala | Leu | Tyr<br>210 | Tyr | Ile | His | Leu<br>215 | Lys | Pro | Lys | Ala | Lys<br>220 | Ser | Leu | Ser | Leu |
| Leu<br>225 | Asp | Glu | Arg | Glu | Glu<br>230 | Ala | Gly | Glu | Gln | Thr<br>235 | Thr | Pro | Thr | Leu | Ser<br>240 |
| Pro | Thr | Leu | Ser | Ala<br>245 | Phe | Gln | Phe | Asn | Glu<br>250 | Lys | Gln | Pro | Thr | Glu<br>255 | Thr |
| Val | Leu | Asn | Ile<br>260 | Pro | Leu | Asn | Leu | Pro<br>265 | Lys | Leu | Pro | Asn | Gly<br>270 | Ser | Lys |
| Glu | Glu | Ser<br>275 | Pro | Ser | Tyr | Asp | Asp<br>280 | Ala | Val | Pro | Leu<br>285 | Arg | Val | His |
| Asp | Ser<br>290 | Ser | Leu | Asn | Leu | Ile<br>295 | Ile | Leu | Ala | Asp | Thr<br>300 | Ser | Gly | Met | Phe |
| Phe<br>305 | Val | Cys | His | Tyr | Tyr<br>310 | Leu | Tyr | Gln | Pro | Met<br>315 | Gln | Ser | Glu | Gln | Arg<br>320 |
| Asp | Val | His | Phe | Ala<br>325 | Tyr | Ser | Val | Thr | Leu<br>330 | Leu | His | His | Gly | Cys<br>335 | Val |
| Val | His | Cys | Val<br>340 | Met | Pro | Gly | Val | Pro<br>345 | Trp | Gln | Lys | Ala | Arg<br>350 | Leu | Leu |
| Arg | Pro | Thr<br>355 | Phe | Ala | Leu | His | Gly<br>360 | Gln | His | His | Leu | Leu<br>365 | Val | Ser | Ser |
| Ala | Phe<br>370 | Phe | Val | His | Leu | Leu<br>375 | Asp | Val | Gly | Leu | Gln<br>380 | His | Glu | Pro | Asn |
| Cys<br>385 | His | Ile | Val | Cys | Ala<br>390 | Ala | His | Asn | Arg | Ser<br>395 | Pro | Asp | Ile | Thr | Gln<br>400 |
| Leu | Val | Pro | Leu | Arg<br>405 | Lys | Trp | Gly | Ala | Leu<br>410 | Ala | Tyr | Asp | Ala | Ala<br>415 | Thr |
| Leu | Asp | Leu | Val<br>420 | Ser | Leu | Ser | Val | Pro<br>425 | Lys | Ser | His | Leu | Ile<br>430 | Glu | Ala |
| Phe | Arg | Asn<br>435 | Asp | Ser | Ser | Leu | Asp<br>440 | Asn | Arg | Ile | Ser | Ile<br>445 | Ile | His | Tyr |

| | | | | | | | | | | | | | | |
|---|---|---|---|---|---|---|---|---|---|---|---|---|---|---|
| Phe | Leu | Phe | Asp | Ser | Asn | Asp | Met | Asp | Val | Leu | Ala | Glu | Leu | Leu | Asn |
| | 450 | | | | 455 | | | | 460 | | | | | | |
| Asn | Ile | Leu | Glu | Arg | Pro | Leu | Ser | Leu | Asp | Thr | Val | Ala | Leu | Leu | Lys |
| 465 | | | | | 470 | | | | 475 | | | | | | 480 |
| Glu | Ala | Leu | Val | Ala | Gly | Ser | Tyr | Ala | Ala | Val | Arg | Gly | Leu | Pro | |
| | | | | 485 | | | | | 490 | | | | 495 | | |
| Glu | Asp | Ala | Lys | Pro | Leu | Met | Arg | Leu | Leu | Pro | Leu | Thr | Thr | Ala | Leu |
| | | | 500 | | | | | 505 | | | | | 510 | | |
| Ala | Ser | Arg | Pro | Ile | Leu | Ala | Lys | Val | Ala | Asp | Ile | Ser | Val | Gly | Leu |
| | | 515 | | | | | 520 | | | | | 525 | | | |
| Ser | His | Glu | Thr | Leu | His | Asn | Thr | Ser | Met | Met | Leu | Leu | Ser | Pro | Gln |
| | 530 | | | | | 535 | | | | | 540 | | | | |
| Gln | Arg | Leu | Ser | Pro | Tyr | Arg | Thr | Asp | Ile | Trp | Thr | Arg | Leu | Trp | Asp |
| 545 | | | | | 550 | | | | | 555 | | | | | 560 |
| Leu | Leu | Asn | Glu | Ser | Ala | Lys | Gln | Glu | Gln | Pro | Arg | Phe | Ser | Ala | Glu |
| | | | | 565 | | | | | 570 | | | | | 575 | |
| Gln | Val | Thr | Glu | Lys | Leu | Ile | Phe | Ser | Leu | Ala | Cys | Tyr | Gln | Pro | Glu |
| | | | 580 | | | | | 585 | | | | | 590 | | |
| Ala | Leu | Ser | Arg | Cys | Thr | Thr | Pro | Leu | Ser | Pro | Asp | Thr | Gly | Thr | Gly |
| | | 595 | | | | | 600 | | | | | 605 | | | |
| Gly | Phe | Gly | Asp | Tyr | Ser | Ser | Gly | Ser | Ala | Phe | Pro | Phe | Ser | Asn | Glu |
| | 610 | | | | | 615 | | | | | 620 | | | | |
| Val | Leu | Pro | Phe | Ile | Glu | Leu | Glu | Gly | Cys | Thr | Ala | Ser | Lys | Gln | Glu |
| 625 | | | | | 630 | | | | | 635 | | | | | 640 |
| His | Val | Ile | Ser | Val | Tyr | Leu | Arg | Glu | Leu | Ser | Val | His | Leu | Val | Lys |
| | | | | 645 | | | | | 650 | | | | | 655 | |
| His | Thr | Ser | Lys | Pro | Asn | Thr | Gly | Phe | Arg | Trp | Leu | Lys | Glu | Thr | Phe |
| | | | 660 | | | | | 665 | | | | | 670 | | |
| Phe | Glu | Arg | Ser | Gln | Ala | Pro | Ala | His | Val | His | Ala | Val | Ala | Ser | Gln |
| | | 675 | | | | | 680 | | | | | 685 | | | |
| Phe | Val | Ser | Ala | Gln | Leu | Glu | Leu | Ser | Arg | Ala | Leu | Cys | Ser | Leu | Val |
| | 690 | | | | | 695 | | | | | 700 | | | | |
| Cys | Arg | Ala | Ala | Gly | Leu | Asp | Ala | Arg | Met | Glu | Thr | Ser | Arg | Gly | Phe |
| 705 | | | | | 710 | | | | | 715 | | | | | 720 |
| Gln | Leu | Ile | Asp | Gln | Met | Ala | Ala | Asn | Gln | His | Ser | Leu | Phe | Leu | |
| | | | | 725 | | | | | 730 | | | | | 735 | |
| Ile | Leu | Glu | Arg | Tyr | Cys | Leu | Ala | Val | Glu | Ser | Ile | Ala | Phe | Pro | Leu |
| | | | 740 | | | | | 745 | | | | | 750 | | |
| Pro | Glu | Gly | Phe | Ser | Ser | Phe | Phe | Thr | Tyr | Leu | Gly | Tyr | Arg | Ala | Leu |
| | | 755 | | | | | 760 | | | | | 765 | | | |
| Gly | Tyr | Asp | Met | Phe | Leu | Gln | Tyr | Val | Glu | Asn | His | Val | Phe | Glu | Leu |
| | 770 | | | | | 775 | | | | | 780 | | | | |
| Gln | Val | Asp | Val | Met | Lys | Ala | Ile | Val | Phe | Asp | Ile | Glu | Asp | Ser | Pro |
| 785 | | | | | 790 | | | | | 795 | | | | | 800 |
| Leu | Gly | Ile | Glu | Arg | Lys | Leu | Ser | Leu | Leu | Ser | Ala | Leu | Pro | Lys | Gln |
| | | | | 805 | | | | | 810 | | | | | 815 | |
| Arg | Ala | Gln | Arg | Leu | Leu | Lys | Cys | Trp | Gln | His | Pro | Asp | Ser | Leu | Met |
| | | | 820 | | | | | 825 | | | | | 830 | | |
| Ile | Arg | Gly | Arg | Glu | His | Ala | Ala | Asn | Ile | Leu | Ser | Gly | Gln | Gln | Gln |
| | | 835 | | | | | 840 | | | | | 845 | | | |
| Glu | Val | Leu | His | Gln | Gln | Arg | Pro | Thr | Ala | Cys | Val | Asn | Gln | Ser | Arg |
| | 850 | | | | | 855 | | | | | 860 | | | | |
| Asn | Asn | Gly | Arg | Ser | Asp | Leu | Thr | Ala | Glu | Ala | Leu | Ser | Pro | Leu | Asp |
| 865 | | | | | 870 | | | | | 875 | | | | | 880 |

-continued

| Ser | Phe | Leu | Asp | Leu | Leu | Thr | Ala | Lys | Ala | Ser | Leu | Asn | Glu | Leu | Asp |
|-----|-----|-----|-----|-----|-----|-----|-----|-----|-----|-----|-----|-----|-----|-----|-----|
|     |     |     |     | 885 |     |     |     |     | 890 |     |     |     |     | 895 |     |
| Tyr | Asn | Leu | Leu | Ile | Glu | Thr | Thr | Leu | Ser | Ser | Ile | Asp | Gln | Leu | Lys |
|     |     |     | 900 |     |     |     |     | 905 |     |     |     |     | 910 |     |     |
| Leu | Glu | Ala |     |     |     |     |     |     |     |     |     |     |     |     |     |
|     |     | 915 |     |     |     |     |     |     |     |     |     |     |     |     |     |